United States Patent
Zhang et al.

(10) Patent No.: US 6,342,378 B1
(45) Date of Patent: Jan. 29, 2002

(54) BIOGASIFICATION OF SOLID WASTE WITH AN ANAEROBIC-PHASED SOLIDS-DIGESTER SYSTEM

(75) Inventors: Ruihong Zhang; Zhiqin Zhang, both of Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/131,010

(22) Filed: Aug. 7, 1998

(51) Int. Cl.⁷ .................................................. C12P 3/00
(52) U.S. Cl. ........................ 435/168; 435/167; 210/203; 210/920
(58) Field of Search ................................ 435/168, 167; 210/603, 920

(56) References Cited

U.S. PATENT DOCUMENTS

| | | | |
|---|---|---|---|
| 3,383,309 A | | 5/1968 | Chandler |
| 4,022,665 A | | 5/1977 | Ghosh et al. |
| 4,168,252 A | * | 9/1979 | Makino ..................... 260/17.5 |
| 4,696,746 A | | 9/1987 | Ghosh et al. |
| 4,735,724 A | | 4/1988 | Chynoweth et al. |

FOREIGN PATENT DOCUMENTS

FR          2443504        11/1978

OTHER PUBLICATIONS

Pohland, F.G. and Ghosh, S., "Developments in Anaerobic Treatment Processes," *Biotechnol. & Bioeng., Symp.* No. 2:85–106 (1971).

Pohland, F.G. and Ghosh, S., "Developments in Anaerobic Stabilization of Organic Wastes—The Two–Phase Concept," *Environmental Letters*1(4):255–266 (1971).

Chynoweth, D.P., et al., "A Novel Process for Anaerobic Composting of Municipal Solid Waste," *Applied Biochemistry and Biotechnology*28/29:421–432 (1991).

Hills and Roberts, "Anaerobic Digestion of Dairy Manure and Field Crop Residues," *Agricultural Wastes*3:179–189 (1981).

Dar, Gh.H., et al., "Biogas Production from Preetreaated Wheat Straw, Lantana Residue, Apple and peach Leaf Litter with Cattle Dung," *Biological Wastes*21:75–83 (1987).

Abdullah, et al., "Digestion and nitrogen conservation in cattle and buffaloes given rice straw with or without molasses," *Journal of Agricultural Science*119–255–263 (1992).

Somayaji and Khanna, "Biomethanation of rice and wheat straw," *world Journal of Microbiology & Biotechnology*10:521–523 (1994).

* cited by examiner

*Primary Examiner*—Irene Marx
(74) *Attorney, Agent, or Firm*—Townsend and Townsend and Crew LLP

(57) ABSTRACT

The present invention provides methods for the generation of methane by a two phase anaerobic phase system (APS) digestion of organic substrates. Also provided is a device for practicing the methods of the invention. The APS-digester system is a space-efficient, high-rate solids digestion system. The APS-digester system consists of one or more hydrolysis reactors and one biogasification reactor.

1 Claim, 25 Drawing Sheets

BIOGASIFICATION OF SOLID WASTE WITH AN ANAEROBIC-PHASED SOLIDS-DIGESTER SYSTEM

FIELD OF THE INVENTION

This invention relates to improved two phase anaerobic digestion having separated hydrolysis and biogasification reactors which convert biomass to desired methane product gas with high efficiency.

BACKGROUND OF THE INVENTION

Anaerobic digestion has been known to stabilize sludge and other predominantly organic materials, and usable product gas, of varying composition, has been obtained from such anaerobic digestion processes. The organic feed mixture which provides the substrate for anaerobic biodegradation can comprise a wide variety of organic carbon sources, ranging from raw sewage sludge to municipal refuse, or biomass material such as plants and crop wastes. The process of anaerobic digestion degrades any of these organic carbonaceous materials, under appropriate operating conditions, to product gas which contains the desirable methane gas.

Anaerobic digestion uses a consortium of natural bacteria to degrade and then convert an organic substrate into a mixture of carbon dioxide and methane. The existing anaerobic digestion systems for organic substrate digestion can be separated into two major types, one phase systems and two phase systems. Existing one phase systems include the batch digester, completely mixed digester and the plug flow digester. These one phase systems, in which the organic substrate and the microorganisms are housed together are easy to operate and of low cost. Completely mixed digesters and plug flow digesters require continuous handling of feedstock and do not operate in batch mode. Further, the biogas produced in one phase systems consists primarily of carbon dioxide in the early stages of digestion. The high carbon dioxide content of the biogas is attributable to the slow growth of the methanogenic microorganisms and their inhibition by high concentrations of volatile fatty acids (VFAs). In order to reduce the inhibition of the microorganisms by the VFAs, the two phase digester has been introduced.

Separated two phase anaerobic digestion systems have been found to enhance the conversion efficiency, such as described in Pohland and Ghosh, *Biotechnol. and Bio-eng. Symp.* No. 2, 85–106 (1971), John Wiley and Sons, Inc. and by the same authors in *Environmental Letters*, 1: 255–266 (1971). A typical two phase anaerobic digester system comprises an acid phase digester and a biogasification reactor. The acid phase digester is usually designed as a solid-bed batch reactor where solid waste is housed and leached soluble compounds are collected. In the acid first phase, the microbial population and operating conditions are selected to promote the conversion of organic carbonaceous materials to carbonaceous materials of lower molecular weight, primarily volatile fatty acids. The liquid and solid effluent from the acid phase is conveyed to a biogasification second phase, where methanogenic organisms convert the volatile fatty acids to product gas that is composed primarily of methane and carbon dioxide. Product gas is removed from the biogasification reactor and processed, or scrubbed, to separate the methane component that is drawn off as pipeline gas.

Two phase anaerobic digestion has been carried out in a single reactor as taught, for example, by U.S. Pat. No. 4,735,724 which teaches a non-mixed vertical tower anaerobic digester and anaerobic digestion process which provides passive concentration of biodegradable feed solids and microorganisms in an upper portion of a continuous digester volume and effluent withdrawal from the middle to the bottom portion of the digester, resulting in increased solids retention times, reduced hydraulic retention times and enhanced bioconversion efficiency.

U.S. Pat. No. 4,022,665 discloses certain specific operating conditions for a two phase anaerobic digestion process, such as feed rates and detention times, which promote efficient conversion of organic materials. Additionally, the '665 patent discloses two separated biogasification reactors, a biogasification reactor I operated in series with a biogasification reactor II. The biogasification reactor II receives effluent fluid and/or effluent gas from biogasification reactor I. A somewhat similar process is disclosed in U.S. Pat. No. 4,696,746 which teaches a process for two phase anaerobic digestion with two discrete biogasification reactors operated in parallel.

U.S. Pat. No. 3,383,309 teaches that the rate and efficiency of the anaerobic digestion process, particularly in the methane forming phase, are increased when hydrogen gas is introduced into the digester sludge. According to the '309 patent, hydrogen gas is introduced into both the acid forming and the methane forming phases, to increase the availability of energy rich "hyper-sludge." All improvements disclosed in U.S. Pat. Nos. 4,022,665, 4,696,746 3 and 383,309 can be adapted for use according to the improved process of the present invention and the teachings of that patent are incorporated herein by reference.

French Patent No. 78 34240 describes an apparatus for biogasification which is known in the art as an upflow sludge blanket reactor. This apparatus utilizes a two-stage digestion apparatus. The apparatus is designed for and uses continuous recirculation between the reactors of the two stages. Continuous recirculation requires a relatively complex apparatus including filters, pumps and manifolded inlets to disperse the recirculated liquid stream and to avoid its "short circuiting directly to the outlet of the reactor into which it was just circulated. Additionally, the continuous recirculation requires two pumps that must operate continuously. In contrast, the present invention utilizes intermittent recirculation.

The sequential batch anaerobic composting (SEBAC) reactor is a relatively new digestion system. See, Chynoweth et al., *Appl. Biochem. Biotech.* 28: 421–32 (1991). The SEBAC system consists of three reactors. Each reactor operates as a single phase batch digester. The three reactors are interconnected and operated on a different digestion schedule, the first being newly started, the second running in the middle of a digestion and the third running toward the end of a digestion. When new feedstock is loaded into the first reactor, the liquid from the third reactor is transferred to the first reactor to inoculate the feedstock and speed-up the digestion process.

A broad range of organic substrates are appropriate feedstocks for biogasification reactors. An exemplary feedstock is agricultural waste. Agricultural waste consists mostly of carbonaceous organic materials and it presents a particularly attractive renewable source of raw material for the generation of methane. The use of agricultural waste for this purpose serves a dual purpose, it produces a useful product and reduces the volume of agricultural waste which must be disposed of Many different types of agricultural waste can be digested utilizing a two phase anaerobic digestion scheme. The waste from the production of rice provides a salient example.

In California, for examples large quantities of rice straw are produced each year as by-products of rice production. In the Sacramento Valley alone, 1,452,000 tons of rice straw were produced in the crop year of 1994–1995 (CARB-CDFA, Progress report on the phase down of rice straw burning in the Sacramento Valley Air Basin, Report To The Legislature, California Air Resources Board and California Department of Food and Agriculture (1995)). Due to lack of feasible conversion technologies, however, utilization of these materials for energy production has not become practical for the agricultural sectors.

Current methods for disposal of these agricultural residue materials have caused widespread public concerns with regard to their environmental impact. In the case of rice and wheat straw disposal, for example, open field burning is considered as a practice causing serious air pollution problems, because of the emissions of smoke and other air pollutants, such as gases, particles and aerosols.

Current California legislation (the Connelly-Areias-Chandler Rice Straw Burning Reduction Act of 1991) mandates the rice growers to phase down burning of rice straw, requiring a reduction in rice straw acreage burning to no more than 25% of the planted acreage or 125,000 acres in the Sacramento Valley by the year 2000, whichever is less. As a result, in 1994–95, about 59% of the rice straw was burned and 38.4% was disposed of in the fields by soil incorporation. Off-farm disposal of rice straw as livestock feed and materials for environmental mitigation and erosion control counted for only 0.6%. Rice growers are under extreme pressure to find alternative environmentally friendly methods for straw disposal and/or utilization. If no other practical straw disposal alternatives are developed to compensate for the burning phasedown, rice farmers will be forced to incorporate an estimated 72.9% of the straw production by the year 2000 to comply with the statutory rice straw burning phasedown requirements. However, available research and experience suggest that incorporation rates this high could potentially cause reduction in crop yield and increase of foliar disease and possible development of adverse soil conditions.

Rice straw is offered as a single relevant example. The disposal of other solid wastes presents similar problems and new economical technologies for solid waste disposal and/or utilization must be developed. Thus, a method for disposing of agricultural and other wastes which utilized an apparatus of simple design, required little expenditure of energy to operate and which produced methane as it reduced the volume of disposable solids would represent a significant advance. Quite surprisingly the present invention provides such methods and devices.

SUMMARY OF THE INVENTION

Anaerobic digestion of solid waste, particularly agricultural waste, is a promising technique for both generating energy and reducing the volume of waste which must be disposed of. The energy generated can be significant. For example, the energy content of a pound of rice straw is about 6,500 Btu (British Thermal Units), and the energy stored in the straw by growing crop each year in the Sacramento Valley is $1.95 \times 10^{12}$ Btu. Thus, it is realistic to consider agricultural waste as a renewable resource for energy generation.

Anaerobic digestion is an enhanced biodegradation process that offers a promising alternative approach for helping solve problems caused by agricultural waste such as the imminent rice straw disposal problems in concentrated rice production regions such as California. Anaerobic digestion uses a consortium of natural bacteria to degrade and then convert a large portion of solid waste into biogas, which is a mixture of methane and carbon dioxide. If captured, biogas can be utilized as a clean fuel for heat and power generation.

Anaerobic phase digestion (APS) is a new type of two phase system. The system employs at least one hydrolysis reactor and a biogasification reactor. In the APS digester system, carbon compounds in the organic substrates are liquefied into VFAs in the hydrolysis reactor. The soluble VFAs produced are transferred to the biogasification reactor at a controlled rate. This allows the maintenance of a stable pH level in the biogasification reactor so that the optimum growth rate of methanogenic bacteria can be achieved. In a first aspect, the present invention provides a process for methane production by two-phase anaerobic digestion of organic material. The process comprises incubating a first mixture having a solid organic component and an aqueous liquid component, under anaerobic conditions, in a hydrolysis digester having an upper portion and a lower portion and containing a hydrolysis means therein. After a first period of incubation, a portion of the liquid component of the first mixture residing in the lower portion of the hydrolysis digester is transferred to a methane phase digester having an upper portion and a lower portion and a methanogenesis means therein. In the methane phase digester, the first mixture is combined with the methanogenesis means to form a second mixture. The second mixture is incubated for a second period of time, generating methane. The second mixture is intermittently agitated, then allowed to remain still for a third period of time. After the third period of time, a portion of the second mixture residing in the upper portion of the methane phase digester is transferred to the hydrolysis phase digester.

The APS-digester system of the invention has innovative design features that allow it to handle the solid organic substrates effectively. The hydrolysis reactor is operated in a batch or semi-batch mode to ease the handling of solid materials, and the biogasification reactor operated continuously to maintain active bacterial culture in the system and to produce biogas at a relatively constant level. The device used in the system of the invention is of simple design and is economical to construct and operate.

In a second aspect, the present invention provides an anaerobic phased solids digester system for methane production. The system comprises a hydrolysis reactor which is separated into upper and lower portions by a perforated support means. The upper portion of the hydrolysis reactor has a hydrolysis reactor liquid inlet and the lower portion has a hydrolysis reactor liquid outlet. The device further comprises a biogasification reactor. The biogasification reactor has a biogasification reactor gas outlet and, optionally, an agitating means. Similar to the hydrolysis reactor, the biogasification reactor has an upper portion and a lower portion. The upper portion has a biogasification reactor liquid outlet and the lower portion has a biogasification liquid inlet.

The hydrolysis reactor and the biogasification reactor are connected via a series of conduits through which liquid from one reactor can be transferred to another reactor. Thus, the device also comprises a first conduit connecting the hydrolysis reactor outlet to the biogasification inlet and a second conduit connecting the biogasification reactor outlet with the hydrolysis reactor inlet.

Other features, objects and advantages of the present invention and its preferred embodiments will become apparent from the detailed description that follows.

DETAILED DESCRIPTION OF THE INVENTION AND PREFERRED EMBODIMENTS

Abbreviations and Definitions

Figure 1A:
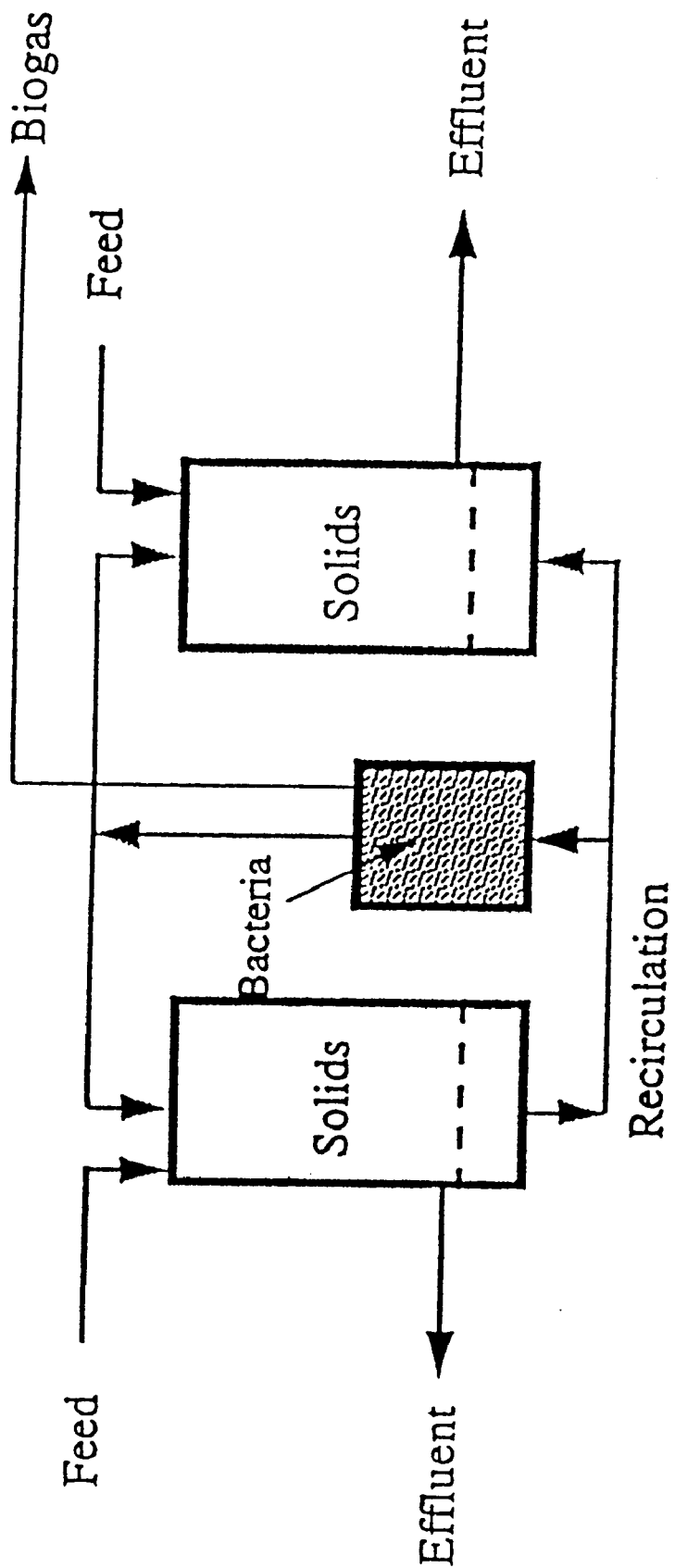
FIG. 1 is a schematic drawing of the anaerobic solids digester system (APS-digester).
Figure 1B:
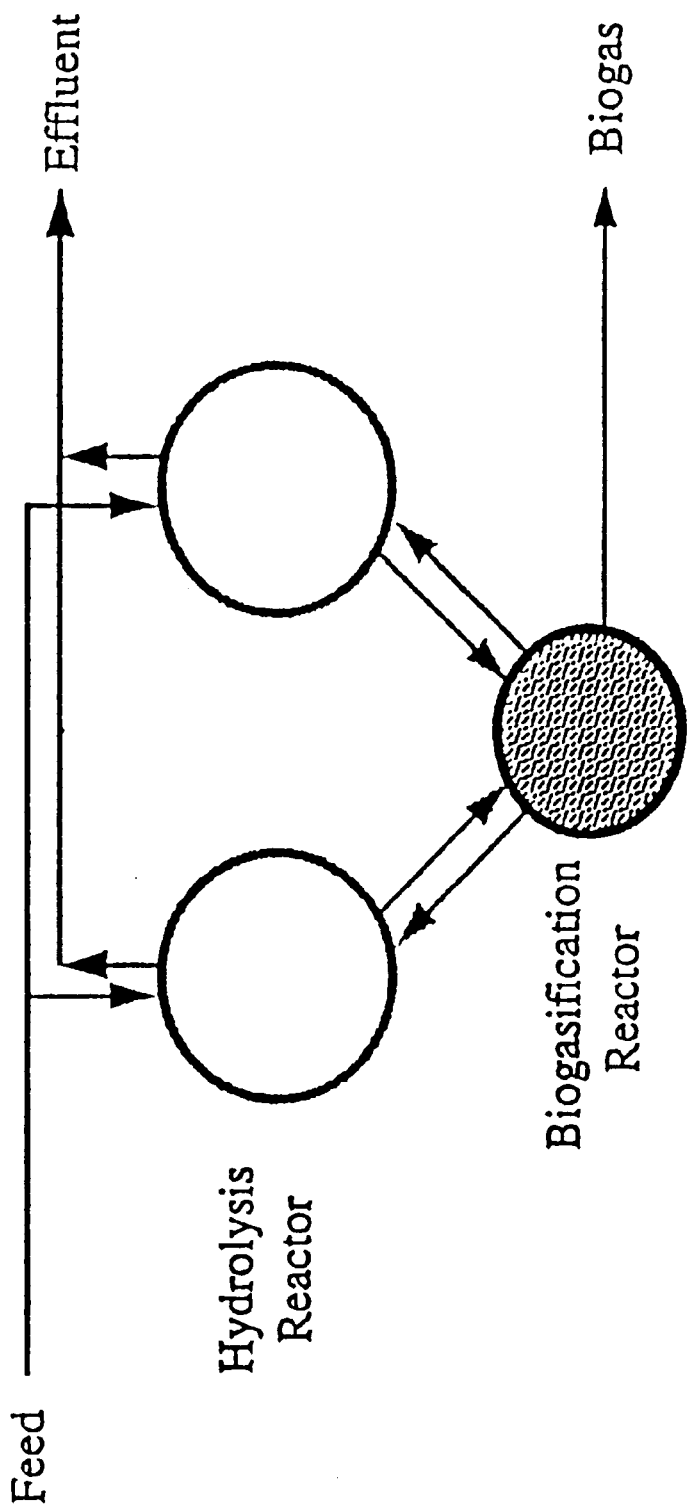

APS, anaerobic phased solids digester; SEBAC, sequential batch anaerobic composition; TS, total solids; VS, volatile solids; SRT, solid retention time; HRT, hydraulic retention time.

As used herein, the term "organic substrate" refers to carbonaceous feedstock which can be used in the process and device of the invention to produce methane.

The terms "biogasification" and "methanogenesis" are used herein essentially interchangeably.

The present invention provides improved methods for the anaerobic digestion of waste to produce methane and devices with which to perform these methods.

Anaerobic phase digestion (APS) is a new type of two phase system. The system employs at least one hydrolysis reactor and a biogasification reactor. In the APS digester system, carbon compounds in the organic substrates are liquefied into VFAs in the hydrolysis reactor. The soluble VFAs produced are transferred to the biogasification reactor at a controlled rate. This allows the maintenance of a stable pH level in the biogasification reactor so that the optimum growth rate of methanogenic bacteria can be achieved. In a first aspect, the present invention provides a process for methane production by two-phase anaerobic digestion of organic material. The process comprises incubating a first mixture having a solid organic component and an aqueous liquid component, under anaerobic conditions, in a hydrolysis digester having an upper portion and a lower portion and containing a hydrolysis means therein. After a first period of incubation, a portion of the liquid component of the first mixture residing in the lower portion of the hydrolysis digester is transferred to a methane phase digester having an upper portion and a lower portion and a methanogenesis means therein. In the methane phase digester, the first mixture is combined with the methanogenesis means to form a second mixture. The second mixture is incubated for a second period of time, generating methane. The second mixture is optionally intermittently agitated, then allowed to remain still for a third period of time. After the third period of time, a portion of the second mixture residing in the upper portion of the methane phase digester is transferred to the hydrolysis phase digester.

The process of the invention can be practiced with any carbonaceous organic substrate including, but not limited to, sewage sludge, forestry waste, food waste, agricultural waste, municipal waste, and the like.

Municipal waste primarily contains cellulosic products, particularly kraft paper. It is known that such cellulosics can be digested as well as the minor amounts of waste protein, carbohydrates and fat present in municipal waste.

In a presently preferred embodiment, the organic substrate consists, at least in part, of an agricultural waste. Agricultural wastes include both plant and animal wastes. Many types of agricultural waste can be used in conjunction with the present invention. Useful agricultural wastes include, but are not limited to, foliage, straw, husks, fruit, manure and the like.

The present invention utilizes a separate acid digestion phase wherein fermentation under anaerobic conditions leads to the production of aldehydes, alcohols and acids. Methane is also generated during this phase. The methane can be collected directly from the hydrolysis phase or it can be routed to the biogasification phase for later routing to a methane collection apparatus. The fermentation in the biogasification phase leads to the production of methane and carbon dioxide. These gases are collected and they can optionally be passed into a clean up zone where the methane and the carbon dioxide are separated. The separator can be any separator known to the art which can separate gas components primarily of carbon dioxide and methane, Both the hydrolysis phase and the methanogenesis phase are operative over variable pH ranges that are related to the nature of the organic substrate and the amount of total solids in the organic substrate. In a preferred embodiment, the acid phase pH is maintained from about 4.5 to about 6.5. In another preferred embodiment, the biogasification phase pH is maintained from about 6.5 to about 7.5.

Any art known hydrolysis or methanogenesis means can be used in the present invention. These include, but are not limited to, acids, bases, enzymes and combinations of these substances. In a presently preferred embodiment, the hydrolysis and methanogenesis means are microorganisms.

Any active hydrolytic or methane producing mesophilic or thermophilic anaerobic digestion system can be used in the present invention. Methane-producing anaerobic systems utilizing acid forming bacteria and methane-producing organisms, as are well known to be employed to produce methane from sewage sludge, can be employed in the practice of the present invention. A review of the microbiology of anaerobic digestion is set forth in Anaerobic Digestion, 1. The Microbiology of Anaerobic Digestion, D. F. Toerien and W. H. J. Hattingh, Water Research, Vol. 3, pages 385–416, Pergamon Press (1969). As set forth in that review, the principal suitable acid forming species include, species from genera including, but not limited to, Aerobacter, Aeromonas, Alcaligenes, Bacillus, Bacteroides, Clostridium, Escherichia, Klebsiella, Leptospira, Micrococcus, Neisseria, Paracolobacterium, Proteus, Pseudomonas, Rhodopseudomonas, Sarcina, Serratia, Streptococcus and Streptomyces. Also of use in the present invention are microorganisms which are selected from the group consisting of *Methanobacterium omelianskii, Mb. formicium, Mb. sohngenii, Methanosarcina barkerii, Ms. methanica* and *Mc. mazei* and mixtures thereof. Other useful microorganisms and mixtures of microorganisms will be apparent to those of skill in the art.

A wide variety of substrates are utilized by the methane producing bacteria, but each species is believed to be characteristically limited to the use of a few compounds. It is therefore believed that several species of methane producing bacteria are required for complete fermentation of the compounds present in certain organic substrates such as sewage. For example, the complete fermentation of valeric acid requires as many as three species of methane producing bacteria. Valeric acid is oxidized by *Mb. Suboxydans* to acetic and propionic acids, which are not attacked further by this organism. A second species, such as *Mb. Propionicum*, can convert the propionic acid to acetic acid, carbon dioxide and methane. A third species, such as Methanosarcina methanica, is required to ferment acetic acid.

An operative mixed culture is capable of sustaining itself indefinitely as long as a fresh supply of organic materials is added because the major products of the fermentation are gases, which escape from the medium leaving little, if any, toxic growth inhibiting products. Mixed cultures generally provide the most complete fermentation action. Nutritional balance and pH adjustments can be made as is known in the art to favor hydrolytic activity As discussed in U.S. Pat. No. 4,022,665, issued May 10, 1977 to Ghosh et al., various studies in the art have demonstrated that a number of acids are converted to methane and carbon dioxide when such acids are contacted with mixed anaerobic cultures. For example, the fermentation of acetic, propionic and butyric acids, as well as ethanol and acetone, all result in the production of methane and carbon dioxide. Only the ratio of methane to carbon dioxide changes with the oxidation level of the particular substrate. Studies in the art have also established that carbon dioxide can be methanted by the oxidation of hydrogen. It has even been suggested that methane fermentation of an acid such, as acetic acid, is a two step oxidation to form carbon dioxide and hydrogen followed by a reduction to form methane. The net result is the formation of methane and carbon dioxide. It has also been advanced that carbon dioxide could be converted to methane in a step-by-step reduction involving formic acid or carbon monoxide, formaldehyde and methanol as intermediates. Whatever the actual underlying mechanism, it is accepted that carbon dioxide can participate in the methanation process. Applicants provide the above discussion as useful background and are not binding themselves to any particular theory of operation.

Mechanical degradation or chemical treatment of the organic substrate may be required either to achieve a particle size appropriate for use in anaerobic digestion according to the invention or to render the carbonaceous components of the organic substrate more accessible to the digestion media Suitable methods of mechanical degradation are known in the art. Various pretreatment of the organic substrate can advantageously be used with the present invention, such as acid or alkaline hydrolysis.

The method also contemplates the selective use of predigestion hydrolysis of the organic substrate before introduction into the organic phase, as well as post biogasification hydrolysis of waste removed from the biogasification phase. The hydrolysis can be conducted as mild acid or mild alkaline hydrolysis, optionally followed by neutralization of the added acid or alkali.

In a presently preferred embodiment, the organic substrate is rice straw. Previous research has demonstrated the feasibility of anaerobically digesting a mixture of straw (rice straw and wheat straw) and other agricultural and food wastes, such as animal manure, green leaves and molasses, using conventional digestion reactors fed in batches or semicontinuously (Hills, D. J. and D. W. Roberts, *Agricultural Wastes* 3:179–189 (1981); Dar, G. H. and S. M. Tandon, *Biological Wastes* 21:75–83 (1987); Adbullah et al, *Journal of Agricultural Sciences* 119:255–263 (1992); Somayaji, D. and S. Khanna, *World Journal of Microbiology & Biotechnology* 10:521–523 (1994)). The research of Hills and Roberts (1981) showed that adding either chopped rice straw or chopped wheat straw to dairy manure enhanced the anaerobic digestion process and increased the methane production.

Rice straw is a ligno-cellulosic material mainly composed of cellulose (37.4%), hemicellulose (44.9%), lignin (4.9%), and silicon ash (13.1%) (Hills, D. J. and D. W. Roberts, *Agricultural Wastes* 3:179–189 (1981)). The straw contains about 0.4% nitrogen and has a carbon to nitrogen ratio (C/N) of around 75. The proper range of C/N ratio for anaerobic digestion is 25–35 (Hills, D. J. and D. W. Roberts, *Agricultural Wastes* 3:179–189 (1981)). Therefore, nitrogen needs to be supplemented in order to effect the anaerobic digestion of rice straw. Nitrogen can be added in inorganic forms, such as ammonia, or in organic forms such as organic nitrogen contained in urea, animal manure or food wastes. But once nitrogen is released from the organic matter, it will become ammonia ($NH_4^+$) which is water soluble. Recycling of nitrogen in the digested liquid will reduce the amount of nitrogen needed for continuous operation of anaerobic digesters. Animal manures and food wastes are good nutrient sources if they are readily available in the areas close to rice straw production. Nitrogen fertilizer, such as ammonia or urea, is another source of nitrogen that can be easily added to the straw and may be more suitable for the areas where handling other types of wastes is not feasible.

Thus, in a preferred embodiment, the organic substrate is supplemented with a nitrogen source. In a further preferred embodiment, the nitrogen source is a member selected from the group consisting of urea, animal manure, food waste, inorganic nitrogen fertilizers and combinations thereof.

Because of its ligno-cellulosic structure, rice straw is difficult to biodegrade. Its major component, cellulose, is a fibrous, water-insoluble substance. It is a linear, unbranched homopolysaccharide of 10,000 to 15,000 d-glucose units in a crystalline structure (Lehninger, A. L. et al., Principles of Biochemistry ($2^{nd}$ ed.), Worth Publishers, New York, N.Y. (1993)). Another major component, hemi-cellulose, is also water-insoluble and consists of a mixture of polymers made up from xylose, arabinose, glucuronic acid and glucose. Breakdown of cellulose and hemi-cellulose through the process of chemical hydrolysis or biodegradation will release simple sugars and make them available for further conversion into other products, such as gases in anaerobic digesters. Lignin is a building component for the cell wall of rice straw and forms the barrier around cellulose and hemi-cellulose. It is a complex aromatic polymer of phenylpropane building blocks and is highly resistant to chemical and biological degradation. Lignin is generally considered not biodegradable in anaerobic digesters although it can be degraded by some aerobic microorganisms, such as fungi (Hobson and Wheatley, 1992). The hydrolysis of cellulose can only occur after the lignin structure is damaged. Enzymes play an important role in biodegradation of lignocellulosic materials. Cellulases, the enzymes that help break down celluloses, can convert cellulose into glucose with little by-products. However, celluloses cannot easily penetrate through the lignin seal surrounding cellulose fibers, and therefore, pretreatment of straw, such as treatment with mechanical grinding and cutting, heat, strong acids or alkaline, are usually helpful.

Several works have been published on chemical pretreatment of rice straw to achieve delignification and hydrolysis of cellulose. The pretreatment methods that have been explored include: bicarbonate treatment (Liu, J. X. et al., *Animal Feed Science and Technology* 52:131–139 (1994)), radiation (Xin and Kumakura, *Bioresource Technology* 43:13–17 (1992)), alkaline peroxide treatment (Patel and Bhatt, *J Chem. Tech. Biotechnol.* 53:53–263 (1991)), and ammonia treatment (Sankat and Lauckner, *Canadian Agricultural Engineering* 33(2):309–313 (1991)).

Thus, in a preferred embodiment, the rice straw is pretreated by a chemical treatment method selected from the group consisting of bicarbonate treatment, alkaline peroxide treatment, radiation treatment, ammonia treatment and combinations thereof.

The ammonia treatment shows several advantages over the other treatment, such as the presence of hydroxyl ions as a delignification factor, a source of nitrogen for biodegradation, and no separate waste water streams generated from the pretreatment process. Thus, in a presently preferred embodiment, the rice straw is treated with aqueous ammonia. In a further preferred embodiment, the ammonia is present in an amount of from about 0.5% to about 10%, more preferably from about 1% to about 5% relative to the total weight of solids derived from rice straw.

Mechanical size reduction of rice straw will also help with the biodegradation by rupturing the cell walls and making the biodegradable components more accessible to microorganisms. Thus in a preferred embodiment, the rice straw is pretreated by a physical process selected from the group consisting of grinding, cutting, heating and combinations thereof. In another preferred embodiment, the rice straw is pretreated using a method comprising grinding the rice straw to a size from about 5 millimeters to about 50 millimeters. In a further preferred embodiment, the rice straw is heated to a temperature of from about 50° C. to about 120° C., more preferably from about 60° C. to about 90° C.

Portions of the liquid component of the digestion mixture are intermittently exchanged between the hydrolysis digester and the biogasification digester during the course of the digestion.

In a preferred embodiment, an amount of liquid from about 10% to about 50% of a digester's liquid content is exchanged between the digesters from 1 to 12 times over a 24 hour period, more preferably from 4 to 6 times in a 24 hour period.

In a second aspect, the present invention provides an anaerobic phased solids digester system for methane production. The system comprises a hydrolysis reactor which is separated into upper and lower portions by a perforated support means. The upper portion of the hydrolysis reactor has a hydrolysis reactor liquid inlet and the lower portion has a hydrolysis reactor liquid outlet. The device further comprises a biogasification reactor. The biogasification reactor has a biogasification reactor gas outlet and an agitating means. Similar to the hydrolysis reactor, the biogasification reactor has an upper portion and a lower portion. The upper portion has a biogasification reactor liquid outlet and the lower portion has a biogasification liquid inlet.

The hydrolysis reactor and the biogasification reactor are connected via series of conduits through which liquid from one reactor can be transferred to another reactor. Thus, the device also comprises a first conduit connecting the hydrolysis reactor outlet to the biogasification inlet and a second conduit connecting the biogasification reactor outlet with the hydrolysis reactor inlet.

In a preferred embodiment, the system of the invention comprises additional hydrolysis reactors. Any number of hydrolysis reactors can be used in conjunction with the present invention. In a preferred embodiment, the system utilizes between 1 and 15 hydrolysis reactors, more preferably between 2 and 8 hydrolysis reactors.

The hydrolysis reactors and the biogasification reactor can be linked in any useful arrangement selected from parallel linking, series linking and combinations thereof. For example, the hydrolysis reactors can be linked in parallel with the biogasification reactor. Alternatively, the hydrolysis reactors can be linked in series with other hydrolysis reactors and this hydrolysis manifold can be linked to the biogasification. In still another embodiment, more than one manifold of hydrolysis reactors can be linked in parallel with the biogasification reactor.

Any perforated support means known in the art can be used in the system of the invention. The support means can comprise structures including, but not limited to, grids, screen, filters, grates, sieves, slats, strainers and the like. The perforated support means can be constructed of any material that is substantially inert under the hydrolysis conditions including, but not limited to, plastics, metals, resin, composites, graphite, and the like. Suitable support means configurations and compositions will be apparent tot hose of skill in the art.

Any means known in the art for agitating a liquid or suspension can be used in the system of the invention. Exemplary means include, but are not limited to, overhead stirrers, gas or motor driven stirrers, magnetic stirrers, shakers, homogenizers, sonicators, gas bubbling tubes, ebulliators and the like. Other useful agitating means will be apparent to those of skill in the art.

The solids feedstock, such as rice straw, and a bacterial culture are contained in the hydrolysis reactor. Each hydrolysis reactor works with semibatches while the biogasification reactor produces biogas continuously. In preferred embodiment, digesting straw, the straw is fed into the hydrolysis reactor from the top of the reactor in batches or semibatches. After the straw is continuously hydrolyzed during each batch treatment, the soluble substances produced in the hydrolysis reactor are transferred intermittently to the biogasification reactor for continuous biogas production. The biogasification reactor contains a concentrated bacterial. After completing a digestion cycle, the digested straw is removed from the hydrolysis reactor before a new batch of straw is added.

The APS-Digester System has innovative design features that allow it to handle the solid organic substrates effectively. The hydrolysis reactor is operated in a batch or semi-batch mode to ease the handling of solid materials, and the biogasification reactor operated continuously to maintain active bacterial culture in the system and to produce biogas at a relatively constant level.

Figure 2:
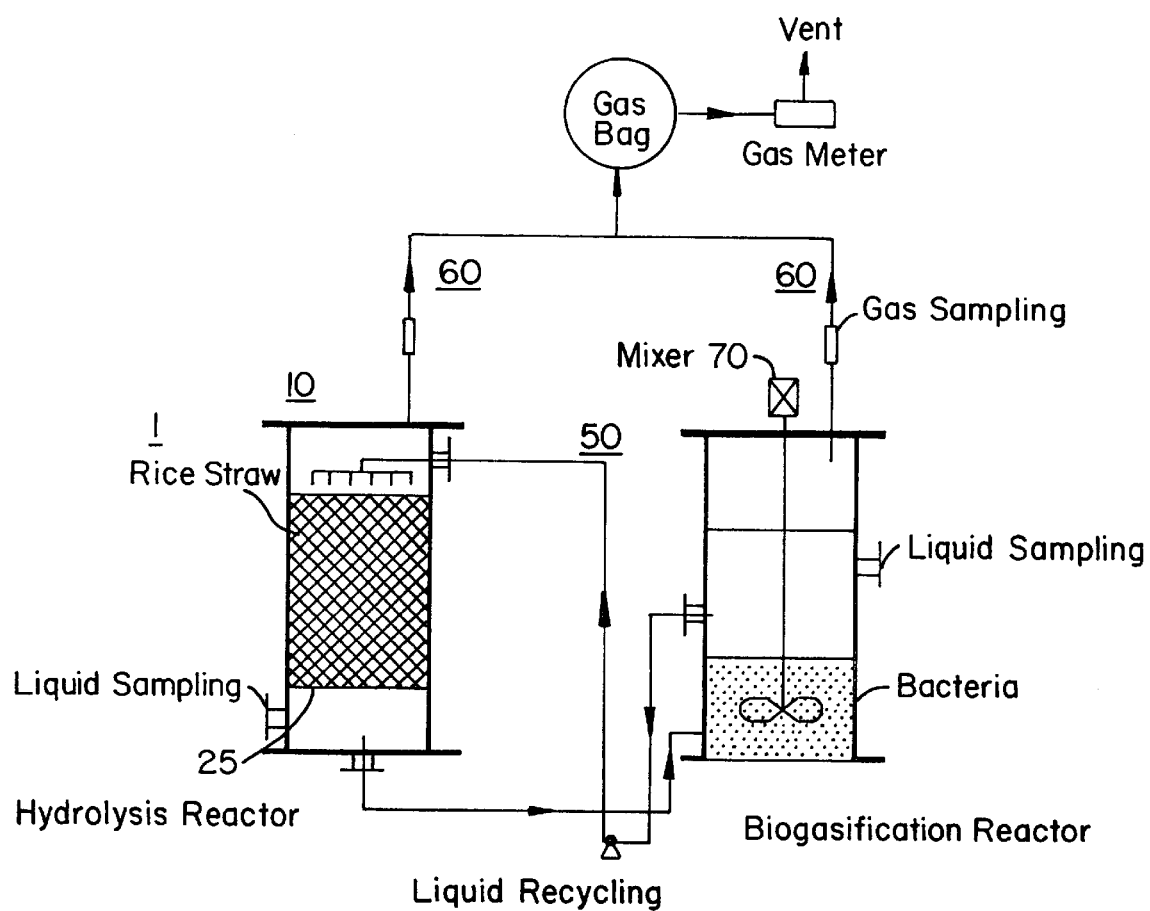
FIG. 2 is a schematic diagram of the laboratory set-up of the APS-digester system.

The operation of the system of the invention will become apparent by reference to FIG. 2. The principle outlined herein with reference to this figure is equally applicable to those systems utilizing additional hydrolysis reactors.

The organic substrate is fed into the hydrolysis reactor 10 through an inlet or the top of the vessel 1. The organic material rests on top of perforated support 25. The hydrolysis reactor contains at least sufficient liquid to wet the organic substrate in the hydrolysis reactor. After a period of incubation in the hydrolysis reactor, the liquid containing the hydrolyzed organic substrate is transferred from the hydrolysis reactor into the biogasification reactor via first conduit 40. This transfer process can be assisted by means of a positive drive pump located inside the hydrolysis reactor, or a negative drive pump located inside the biogasification reactor or along the conduit 40. The mixture in the biogasification reactor is optionally intermittently agitated with an agitating means 70. Following a period of incubation and digestion in the biogasification reactor, the liquid containing the digested organic substrate can optionally be recirculated back into the hydrolysis reactor via second conduit 50. This recirculation can be assisted by a pump as described above, with the caveat that the fluid flow is in the opposite direction, thus, the pumping direction must be similarly shifted. During the period of incubation in the biogasification reactor, the digesting organic substrate gives rise to a gaseous methane-containing product which is vented through the biogasification reactor gas outlet 60. When the methane generating potential of the organic substrate has been exhausted, the remaining material is removed through an outlet or the top of reactor 10.

In operation, withdrawing the liquid from the bottom of the hydrolysis reactor prevents disturbing the organic substrate hydrolysis process proceeding in the upper portion of the hydrolysis reactor.

The following examples further define the invention and should not be construed as fisher limiting. The contents of all references, patents and patent applications cited throughout are expressly incorporated herein by reference.

The detailed examples which follow illustrate the device and methods of the invention as applied to the production of biogas from the digestion of rice straw.

EXAMPLES

Example 1 illustrates the method and the device of the invention in conjunction with the digestion of rice straw.

Example 2 sets forth a comparative study between the device and the method of the invention and other art recognized methods of digesting organic substrates. Similar to Example 1, Example 2 utilizes rice straw as an exemplary organic substrate.

Example 1

1.1 Experimental Materials and Methods

Two laboratory scale APS-Digester Systems were used for this study. One system had one hydrolysis reactor and one biogasification reactor as shown in FIG. 2, and the other had two hydrolysis reactors and one biogasification reactor. All the reactors were made of plexiglas with inside diameters of 4.5 inches. The total and working volumes of each reactor were 5.2 L and 4.0 L, respectively. The rice straw was processed in batches, i.e. the system was operated in a batch mode with a retention time of 24 days. During the digestion, liquid was circulated intermittently between the hydrolysis reactor and the biogasification reactor to transport the soluble substances from the hydrolysis reactor to the biogasification reactor. After each batch of treatment, the residual solids were removed from the hydrolysis reactor and a new batch of rice straw was loaded. All the reactors were heated to a constant temperature of 35° C with a circulated and heated water jacket. The hydrolysis reactor was not mixed while the biogasification reactor was mixed intermittently (1 minute every 2 hours) by a mechanical mixer.

Each reactor was connected to a gas collection bag and a wet-tip gas meter which was used to record the daily biogas production volume. Gas samples were taken twice a week from the sampling port on the gas collection line of each reactor and analyzed for the contents of methane and carbon dioxide using a Gas Chromatograph (GC) equipped with a thermal conductivity detector (TCD). The liquid samples were taken from each reactor and measured for pH using a pH meter to monitor the stability of the reactors. For each batch digestion, samples of straw before and after digestion and samples of the reactor contents before and after digestion were taken and analyzed vent for total solids (TS), volatile solids (VS), and pH. The analysis procedures of TS and VS followed the standard methods (APHA, 1992). The reductions of TS and VS in the straw after digestion were calculated using the mass balance method. The reductions of TS and VS, daily biogas production, and total biogas production during the 24 day period were used to evaluate the performance of the digester system under different operational conditions. A total of 17 runs were conducted including three repetitions. All the digestion runs were at a temperature of 35° C. and a retention time of 24 days. The biogasification reactor was initially seeded with the sludge taken from an anaerobic digester in the municipal waste water treatment plant of Davis, Calif.

To study the changes of elemental components in the rice straw during the anaerobic digestion, the solid and liquid samples of three batch treatments were analyzed for various elements including nitrogen (N), phosphorus (P), potassium (K), sulfur (S), calcium (Ca), chloride (Cl), magnesium (Mg), silicon (Si), sodium (Na) and carbon (C). The chemical analysis was conducted by the analytical laboratory of Division of Agriculture and Natural Resources (DANR) at the University of California at Davis (UC Davis). The changes of the elemental composition of the straw after the digestion were calculated using the mass balance method.

Effects of different pretreatment methods, including physical (mechanical), thermal, and chemical (ammonia) treatment, on the digestion of rice straw were investigated. The physical pretreatment included grinding the straw into two lengths (10 mm and 25 mm) with a hammer mill and chopping the straw into one length (25 mm) with a cutter. Thermal treatment was conducted by heating the straw in a pressure cooker for two hours at three different temperatures (60° C., 90° C. and 110° C.). Tap water was added to the straw in 6 to 1 weight ratio prior to the thermal treatment. Chemical treatment was carried out with 58% ammonia hydroxide solution. Only one ammonia treatment level was used for all the digestion runs. The amount of ammonia added to the straw for each digestion run was 2% based on the dry weight of the straw digested. This level was determined based on the adjustment of C/N ratio of the treated straw to around 25. This level of ammonia treatment was also found to be effective for increasing the digestibility of rice straw in an in vitro digestibility study of Sankat and Lauckner (1991). A list of digestion runs operated under a combination of different pretreatment conditions are listed in Table 1.

TABLE 1

| | Pretreatment Conditions | | | |
|---|---|---|---|---|
| Run | Physical Size of Straw | Thermal Temperature | Chemical Ammonia (%)* | Solids Loading Rate (g/L) |
| 1 | 25 mm (ground) | no treatment | 2 | 50 |
| 2 | 25 mm (ground) | 60° C. | 2 | 50 |
| 3 | 25 mm (ground) | 90° C. | 2 | 50 |
| 4 | 25 mm (ground) | 110° C. | 2 | 50 |
| 5 | 10 mm (ground) | 90° C. | 2 | 50 |
| 6 | 25 mm (ground) | 90° C. | 2 | 50 |

TABLE 1-continued

Pretreatment Conditions

| Run | Physical Size of Straw | Thermal Temperature | Chemical Ammonia (%)* | Solids Loading Rate (g/L) |
|---|---|---|---|---|
| 7 | 25 mm (chopped) | 90° C. | 2 | 50 |
| 8 | whole | 90° C. | 2 | 50 |
| 9 | 25 mm (ground) | no treatment | 2 | 50 |
| 10 | 25 mm (chopped) | no treatment | 2 | 50 |
| 11 | whole | no treatment | 2 | 50 |
| 12 | 25 mm (chopped) | no treatment | 2 | 50 |
| 13 | 25 mm (chopped) | no treatment | 2 | 75 |
| 14 | 25 mm (chopped) | no treatment | 2 | 100 |

*Ammonia addition was % of dry weight of rice straw loaded into the hydrolysis reactor.

Three digestion runs (3, 10 and 11) were repeated to validate the testing procedures used in this study. After finding the difference between the repetitions was less than 5%, all the other digestion runs were carried out as a single run for each pretreatment condition in order to save the time for laboratory operations.

1.2 Results

1.2a Characteristics of Rice Straw

Rice straw was collected in bales from a county in northern California and transported to the laboratory. The characteristics of raw rice straw are presented in Table 2.

TABLE 2

| C (%) | N (%) | P (%) | K (%) | H (%) | S (%) | TS (%) | VS (%) | Ash (%) |
|---|---|---|---|---|---|---|---|---|
| 34.80 | 0.46 | 0.09 | 1.58 | 4.61 | 0.14 | 92.12 | 79.50 | 20.50 |

Note: The contents of C, N, P, K, H, S, VS and ash were calculated as the percentage of TS.

1.2b Effects of Thermal Pretreatment

The temperature used for pretreatment did have a significant effect on the digestibility of rice straw as shown in Table 3 with regards to solids (TS and VS) reduction and biogas production. A higher temperature resulted in higher conversion rates of solids and higher biogas production. As compared with non-pretreatment, the TS and VS reductions were increased by 3.4 22.4% and 3.6–22.6%, respectively, and the biogas yield increased by 2.5–17.5% when pretreatment temperature varied from 60° C. to 110° C. The temperature effect was not linear, however. The increase of solids reduction (15.6%) and biogas production was more significant when the temperature increased from 60° C. to 90° C.

Figure 3:
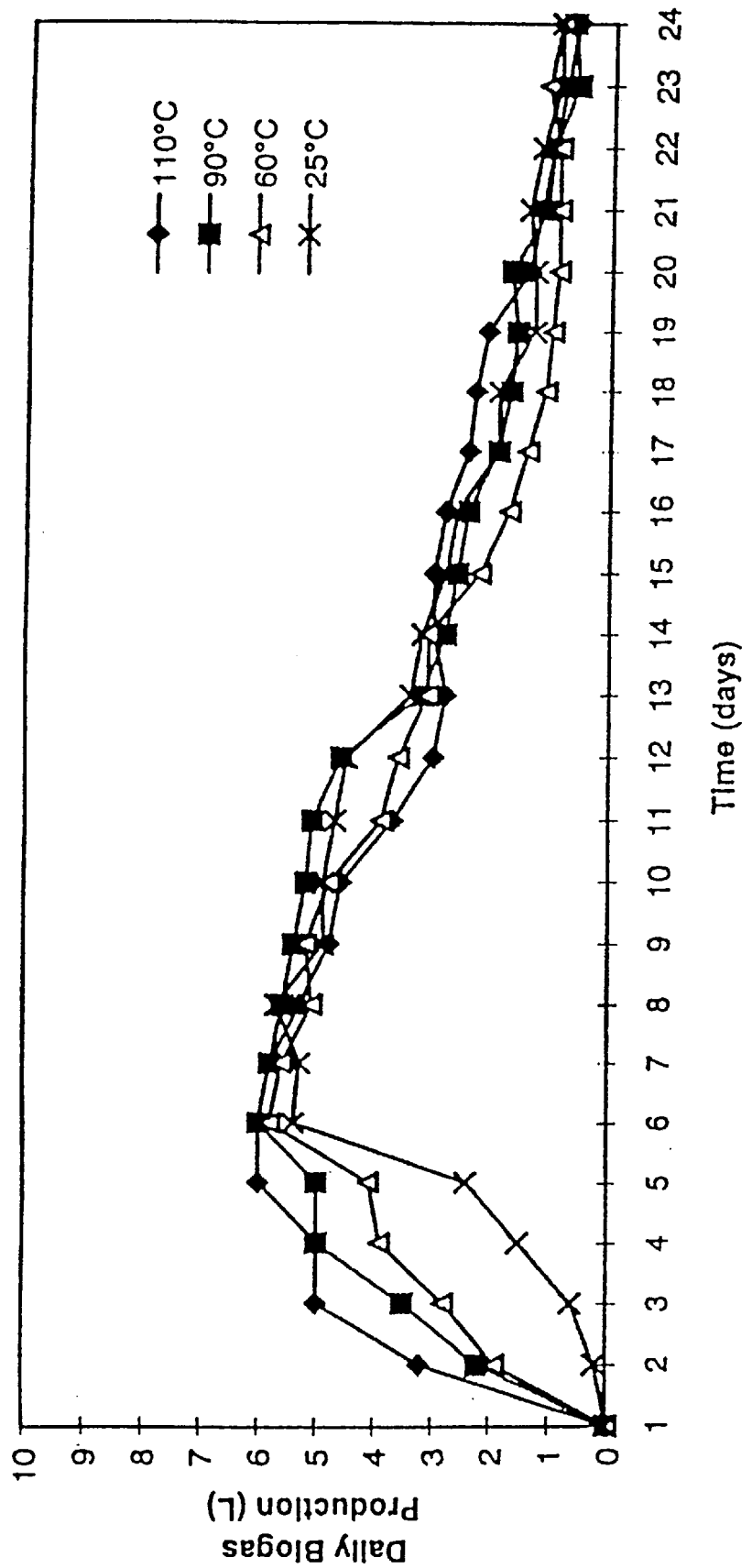
FIG. 3 displays the daily biogas production at different pretreatment temperatures.
Figure 4:
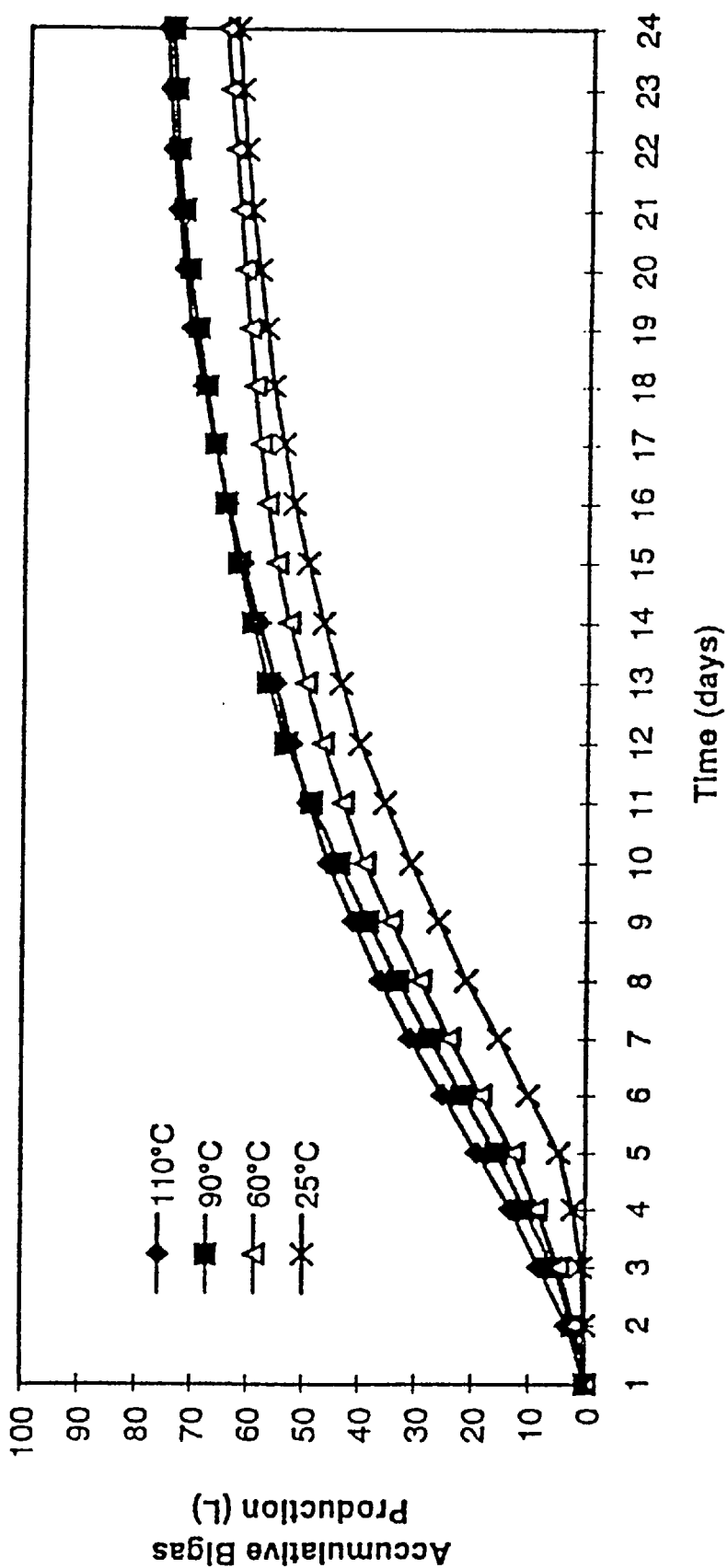
FIG. 4 displays the accumulative biogas production at different pretreatment temperatures.
Figure 5:
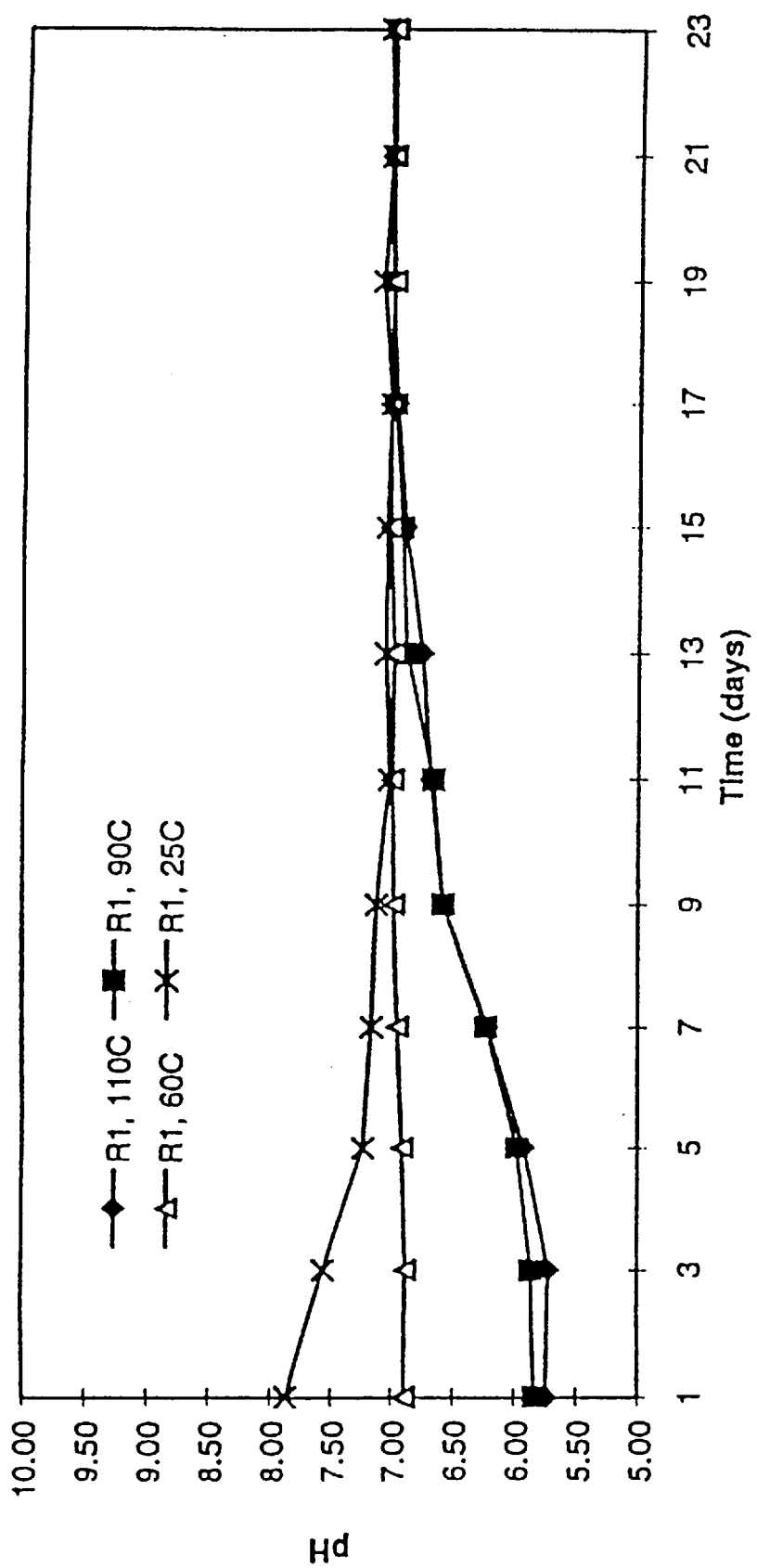
FIG. 5 displays the pH variation in the hydrolysis reactor during the digestion period for different pretreatment temperatures.
Figure 6:
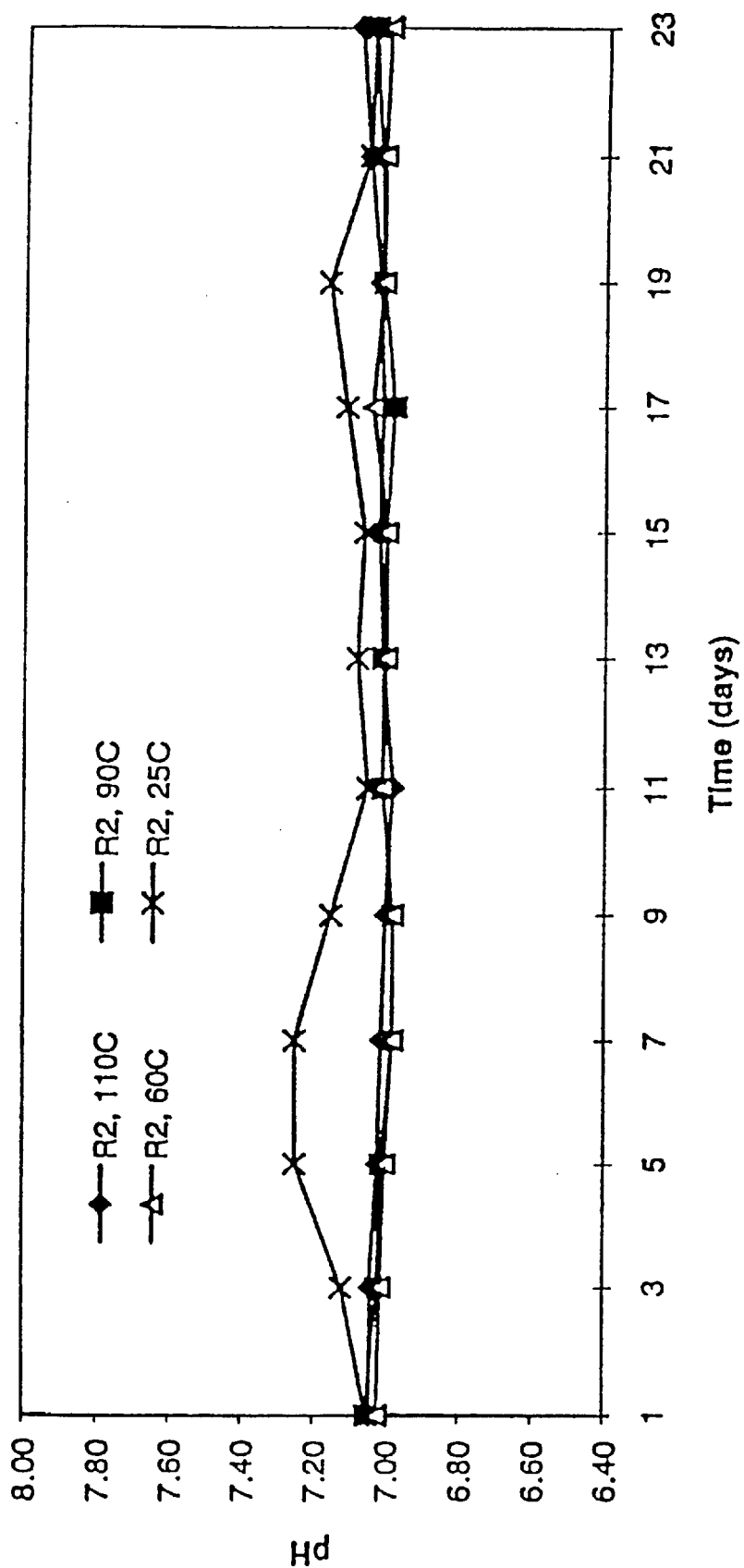
FIG. 6 displays the pH variation in the biogasification reactor during the digestion period at different pretreatment temperatures.

The positive temperature effect may be explained by the increased chemical reaction rate between the components of rice straw and ammonia hydroxide which was added prior to heating. More soluble compounds were released from the straw during the thermal treatment process at higher temperatures and made available to subsequent bacterial degradation. This is clearly reflected by the daily biogas production data as shown in FIG. 3. A higher pretreatment temperature resulted in higher daily biogas production rate during the first six days of digestion. FIG. 4 shows the accumulative biogas production for different pretreatment temperatures. Higher pretreatment temperatures resulted in more acid production and lower pH levels initially in the hydrolysis reactor as shown in FIG. 5. The initial pH was below 6.0 for 90° C. and 110° C. pretreatment. As digestion progressed and acids were transported to and consumed in the biogasification reactor, the pH of the hydrolysis reactor was slowly increased to the neutral level (around 7.0). The pH level of the biogasification reactor for all pretreatment temperatures was maintained relatively constant throughout the digestion as shown in FIG. 6. Therefore, the biogasification reactor provided both chemical and biological buffering capacities for the hydrolysis reactor, making the digester system stable in operation.

TABLE 3

| Pretreatment Temperature (° C.) | TS Reduction (%) | VS Reduction (%) | Total Biogas Production (L) | Biogas Yield] (L/g VS fed) | Methane Content of Biogas (%) |
|---|---|---|---|---|---|
| No treatment | 40.6 | 48.4 | 63.5 | 0.40 | 49.4 |
| 60° C. | 44.0 | 52.0 | 65.3 | 0.41 | 49.9 |
| 90° C. | 59.6 | 67.6 | 74.2 | 0.46 | 51.4 |
| 110° C. | 63.0 | 71.0 | 75.4 | 0.47 | 52.1 |

From the biogas production data as shown in FIGS. 3 and 4, we can see that the digestion process slowed down after two weeks when the hydrolysis of straw and release of soluble sugars became the limiting step. About 75–80% of the biogas was produced in the first two weeks. This implies that if the retention time for a digestion system is designed to be 14 days instead of 24 days, the digester size can be reduced by 42% for a sacrifice of 21–25% biogas production.

1.2c Effects of Physical Pretreatment

Figure 7:
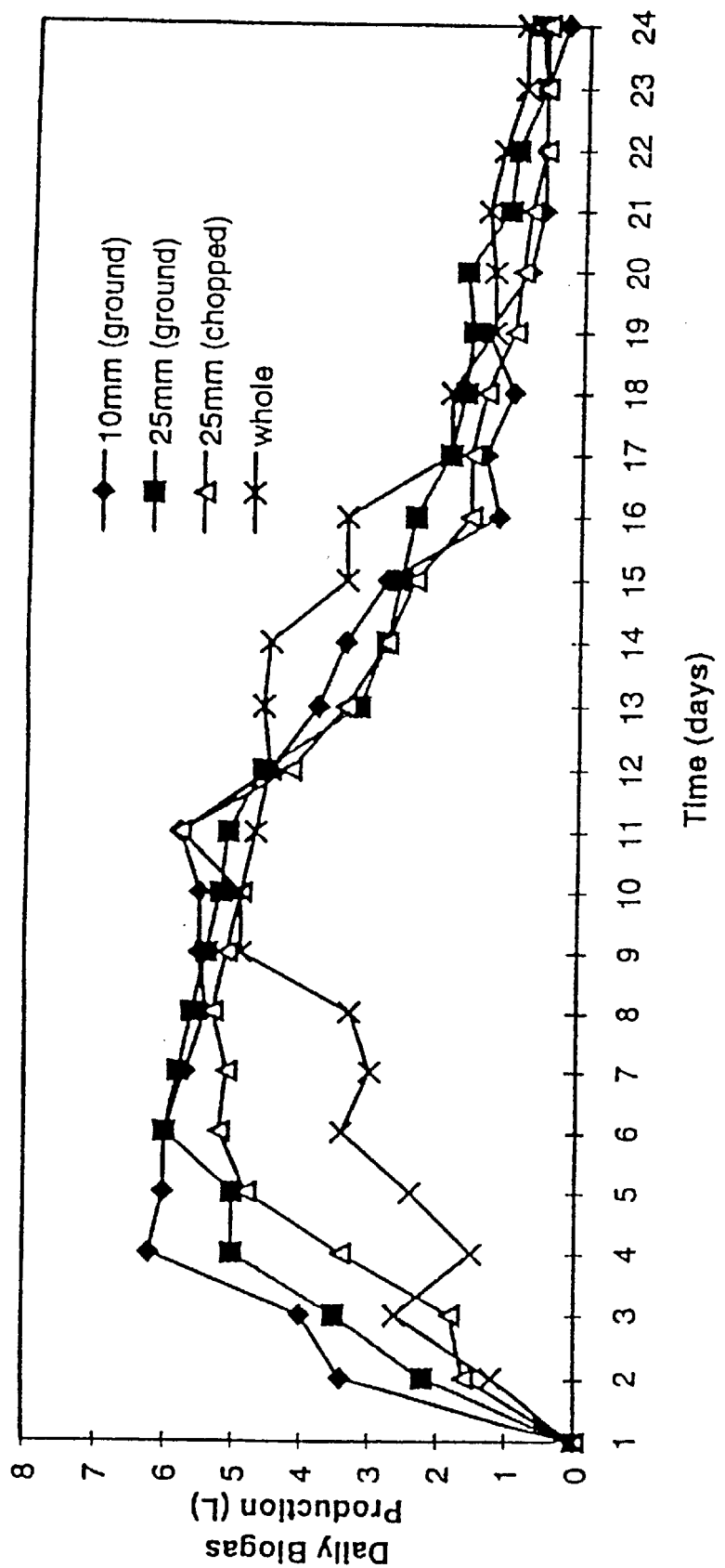
FIG. 7 displays the daily biogas production for different physical pretreatment conditions with thermal pretreatment at 90° C.

Table 4 shows the effects of size reduction of rice straw by mechanical processing (grinding or chopping) on the solids reduction and biogas production. Generally speaking, the smaller the straw particles were, the better the digestion was, i.e. the more solids reduction was and the higher the biogas yield was. Grinding yielded the best digestion results, because milling broke up the cell walls of straw better than chopping alone and made the inside of the straw more accessible for chemical and biological breakdown. Such effects of size reduction are clearly shown in the daily biogas production data (FIG. 7). More soluble sugars were available in the reactors during the initial nine days, yielding a higher biogas production rate, if the straw was processed into smaller particles.

Figure 8:
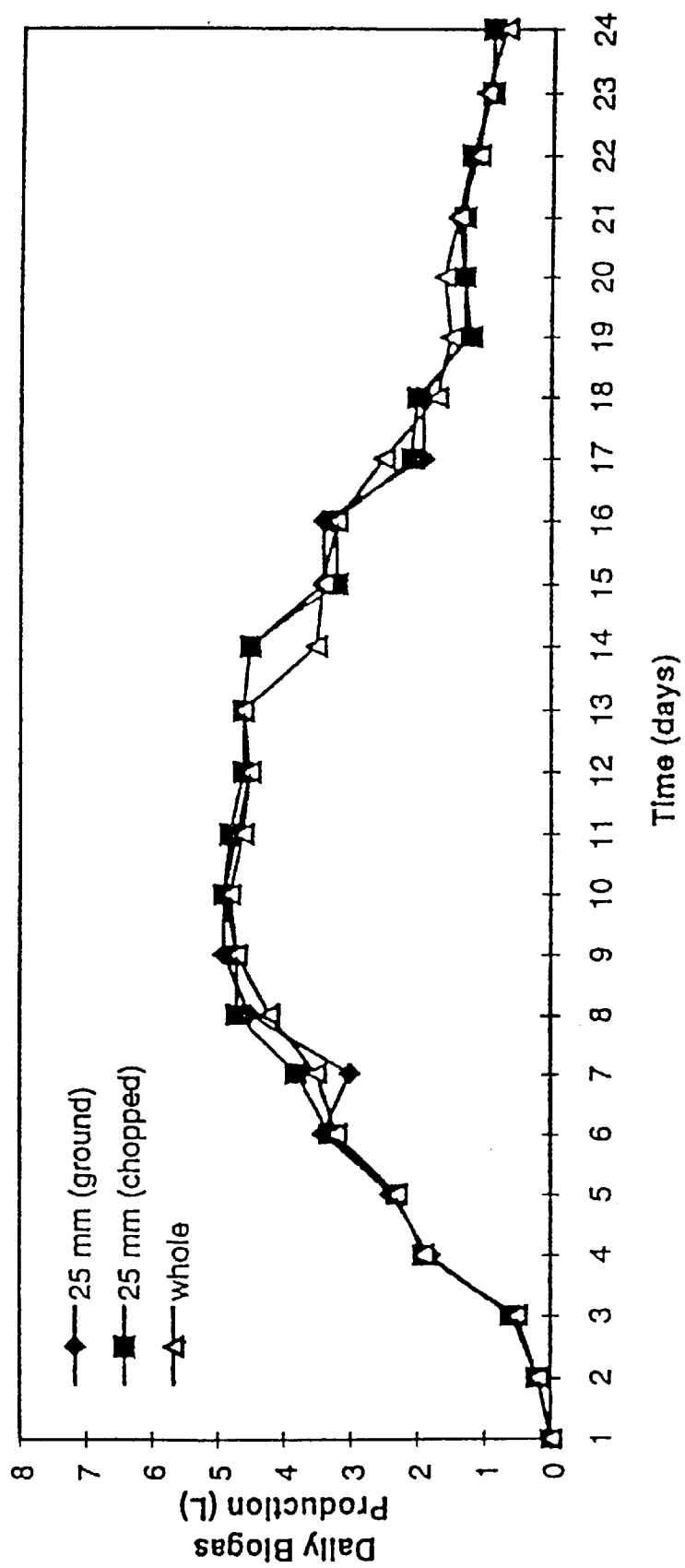
FIG. 8 displays the daily biogas production for different pretreatment conditions without thermal pretreatment.
Figure 9:
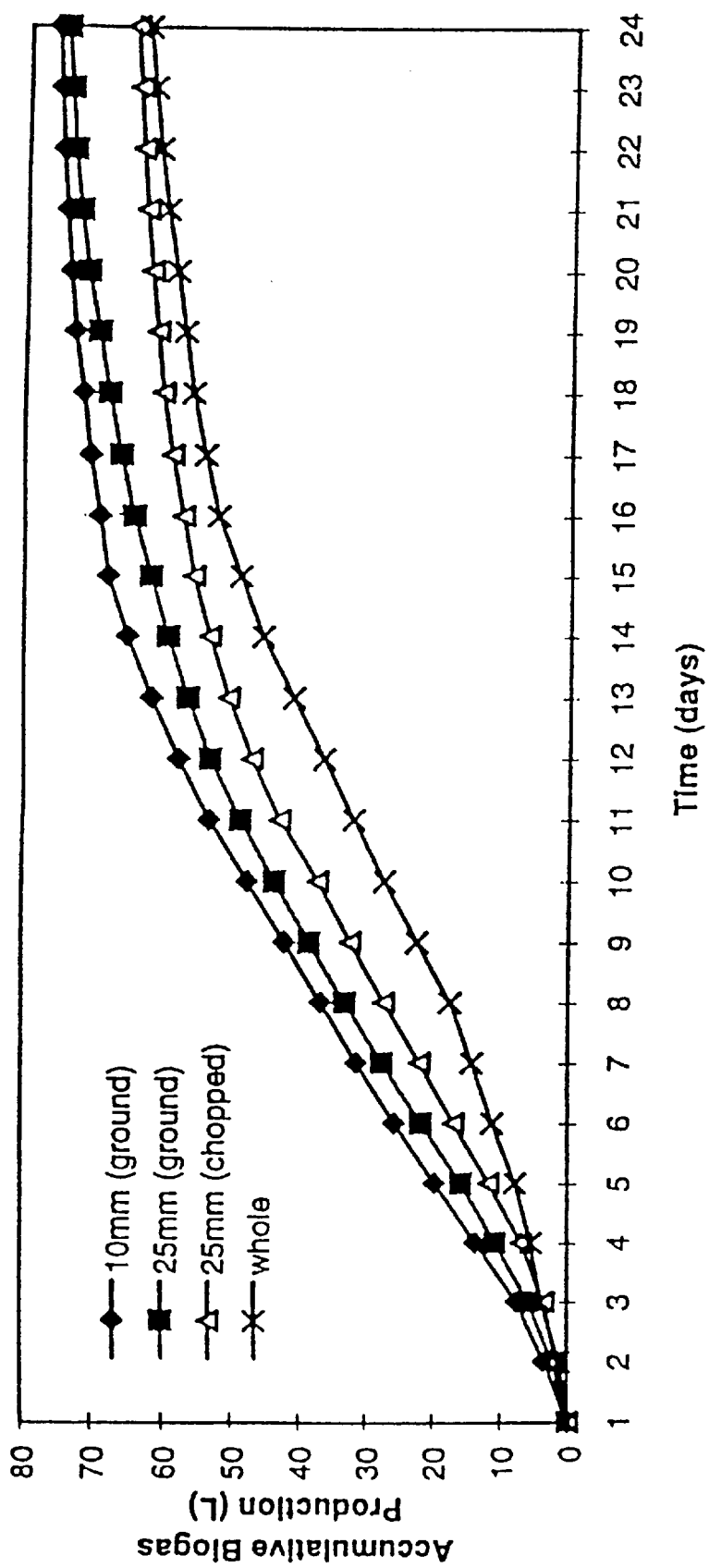
FIG. 9 displays the accumulative biogas production of rice straw for different physical pretreatment.
Figure 10:
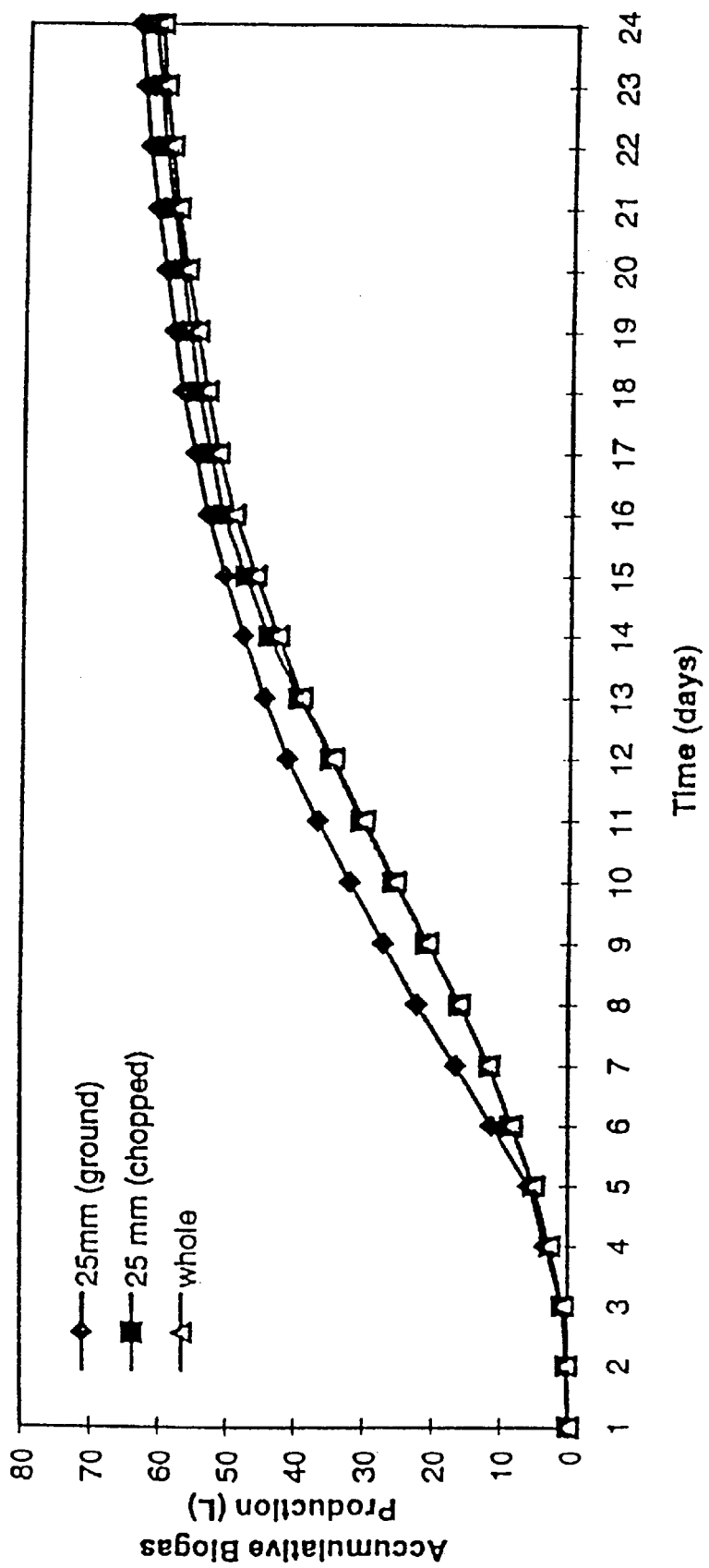
FIG. 10 displays the accumulative biogas production for different physical pretreatment without thermal pretreatment.
Figure 11:
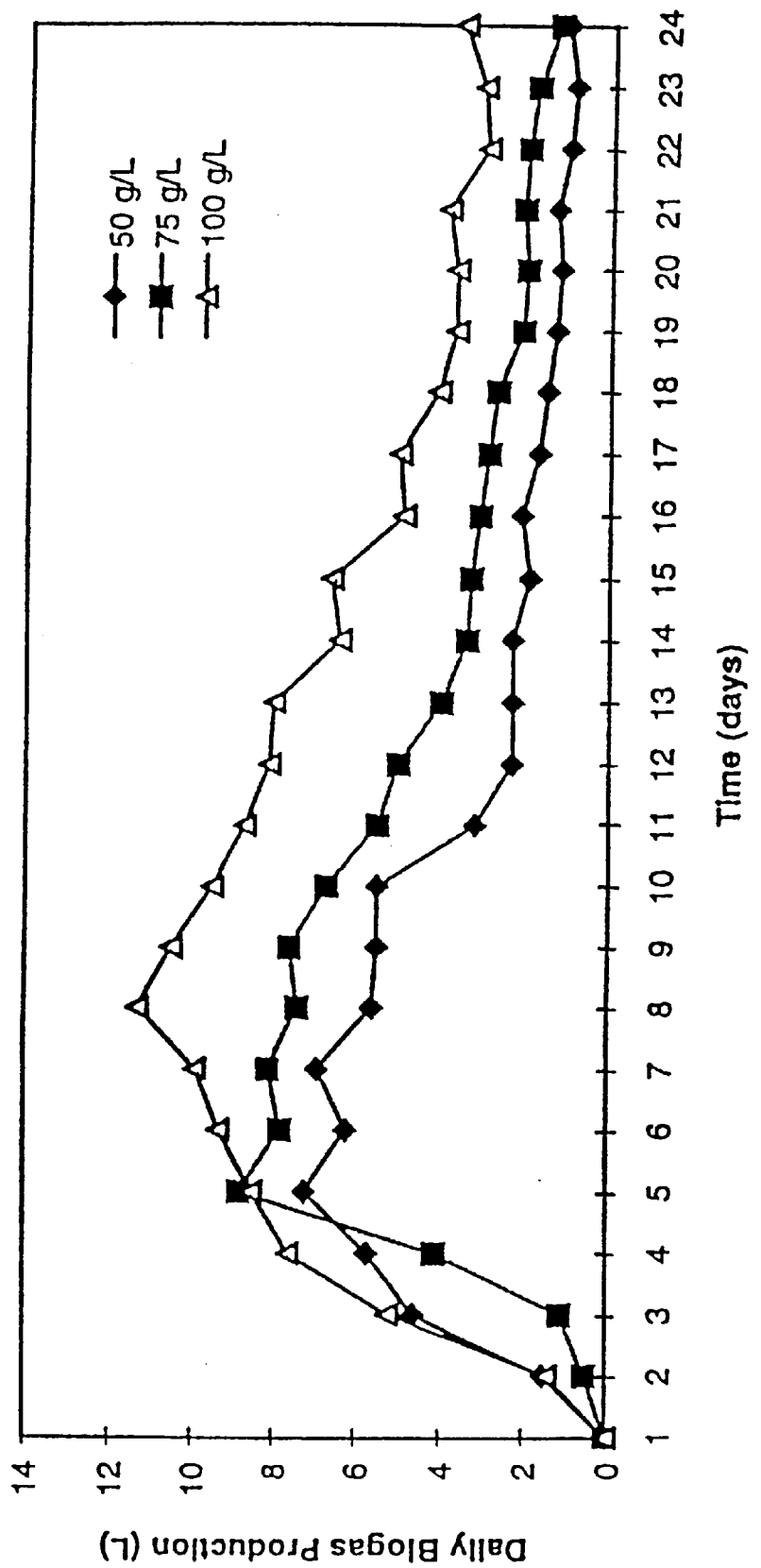
FIG. 11 displays the daily biogas production of rice straw with different solids loading rates.
Figure 12:
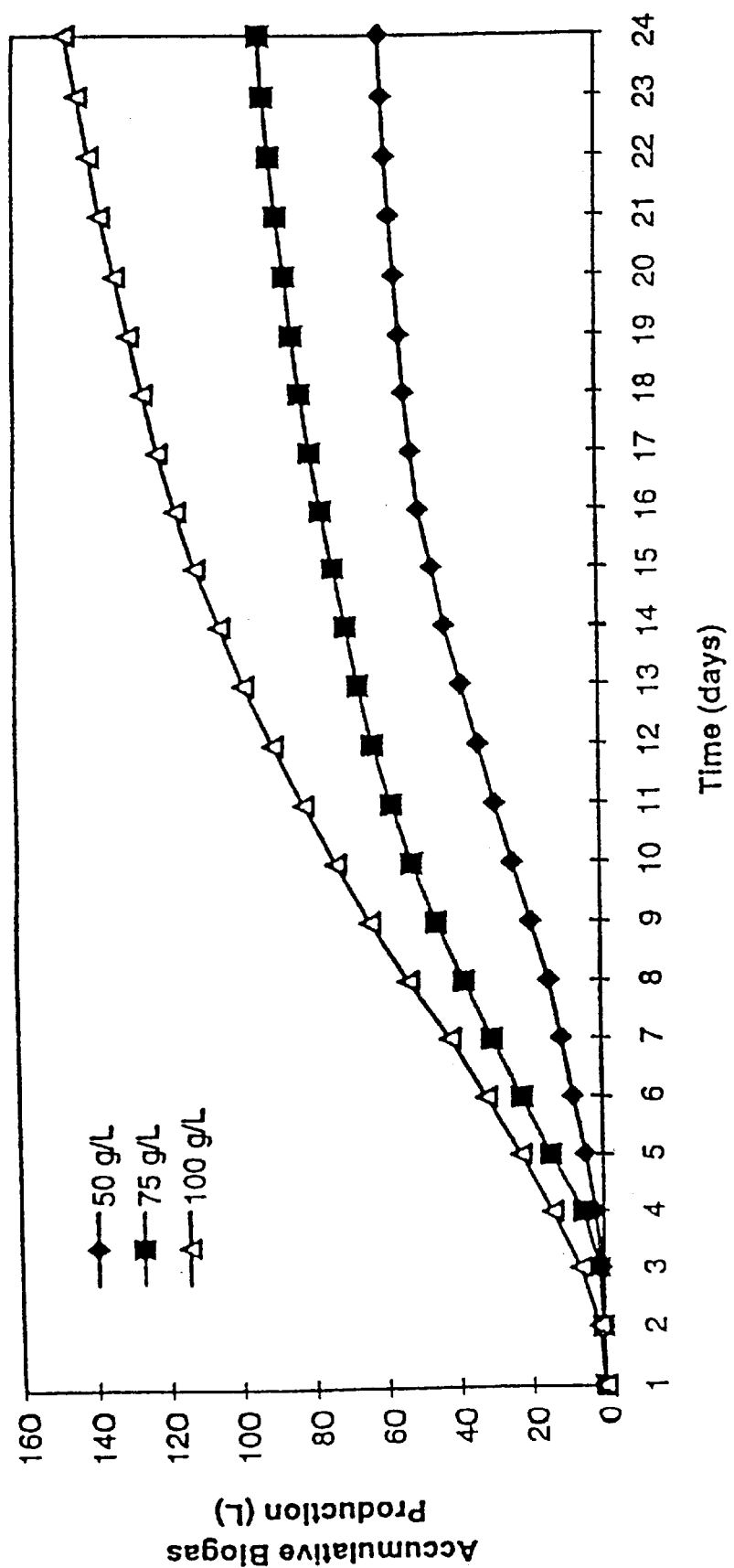
FIG. 12 displays the accumulative biogas production of rice straw for different solids loading rates.

Size reduction appears to have more significant effects when combined with thermal pretreatment than without thermal pretreatment. The biogas yield of ground, 10 mm, thermally pretreated straw was 0.47 L/g VS fed, which is 17.5% higher than the yield of thermally pretreated whole straw (0.40 L/g VS fed). If comparing the ground straw with the chopped straw, we noticed that the biogas yield of ground, 25 mm, thermally pretreated straw was 0.46 L/g VS fed, 12.2% higher than chopped, 25 mm, thermally pretreated straw. The chopped straw was very close to the whole straw for the digestion, showing only 2.5% increase in the biogas yield. Improvement of digester performance by mechanical processing (milling and chopping) was very small if the straw was not thermally pretreated. The digestion rates of these three straws were very close as shown in FIG. 8. FIGS. 9 and 10 show the accumulative biogas production of rice straw for different physical pretreatment conditions with and without thermal pretreatment.

TABLE 4

| Physical Pretreatment (Size of straw) | Thermal Pretreatment (° C.) | TS Reduction (%) | VS Reduction (%) | Biogas Yield (L/g VS fed) | Methane Content of Biogas (%) |
|---|---|---|---|---|---|
| 10 mm (ground) | 90 | 62.4 | 69.6 | 0.47 | 51.1 |

TABLE 4-continued

| Physical Pretreatment (Size of straw) | Thermal Pretreatment (° C.) | TS Reduction (%) | VS Reduction (%) | Biogas Yield (L/g VS fed) | Methane Content of Biogas (%) |
|---|---|---|---|---|---|
| 25 mm (ground) | | 59.6 | 67.6 | 0.46 | 50.6 |
| 25 mm (chopped) | | 44.8 | 60.0 | 0.41 | 50.1 |
| Whole | | 43.0 | 56.4 | 0.40 | 50.0 |
| 25 mm (ground) | None | 40.6 | 48.4 | 0.40 | 49.4 |
| 25 mm (chopped) | | 37.3 | 43.8 | 0.38 | 50.0 |
| Whole | | 36.3 | 42.4 | 0.38 | 50.5 |

1.2d Effects of Total Solids Loading Rate

All the results reported as above were obtained from the digestion runs with the same total solids (TS) loading rate in the hydrolysis reactor of 50 g/L. Potential of increasing the solids loading rate was investigated with three levels of TS loading rate, 50 g/L, 75g/L and 100 g/L, with the chopped, 25 mm, not thermally pretreated straw. A higher solids loading rate means a smaller digester system for treating a given amount of rice straw.

Table 5 shows the solids reduction and biogas production for three solids loading rates. The digester system performed better at a higher loading rate. When the loading rate was increased from 50 g/L to 100 g/L, the solids reduction and biogas yield increased by about 10%. The initial concentration of bacterial mass as measured by the mixed liquor volatile suspended solids (MLVSS) in the biogasification reactor was controlled at 1.2% for all the three loading rates. A higher biogas yield at a higher loading rate means that the capacity of bacteria in the reactors was better utilized at a higher loading rate. Future research will study the optimum food to microorganism ratio (F/M) in the system for different solids loading rates.

TABLE 5

| TS Loading Rate (g/L) | TS Reduction (%) | VS Reduction (%) | Biogas Yield (L/g VS fed) | Methane Content of Biogas (%) |
|---|---|---|---|---|
| 50 | 35.8 | 43.8 | 0.38 | 50.0 |
| 75 | 37.3 | 44.9 | 0.39 | 49.4 |
| 100 | 40.1 | 48.4 | 0.42 | 50.5 |

1.2e Changes of Elemental Composition of Rice Straw During Anaerobic Digestion

Table 6 lists the contents of elemental components in rice straw before and after digestion as obtained from the digestion run with ground, 25 mm straw thermally pretreated at 60° C. The contents of both N and P in the rice straw increased after the digestion. The N content of straw residue from the digester was twice as much as the N content of raw straw. This is beneficial for use of such straw residues as soil amendment because of increased nutrient contents and reduced carbon contents as compared with raw rice straw. The contents of all the other elements as listed in the table decreased after the digestion. The contents of K, Cl, and S were reduced by 90%, 87%, and 43%, respectively. These three elements, together with silicon (Si) are the major problematic elements for combustion of rice straw, causing slagging and fouling of the boilers (Jenkins, B. M. et al. *Biomass and Bioenergy* 10(4):177–200 (1995)). Reduction of these elements through anaerobic digestion will make the straw residues a more desirable biomass fuel for combustion. Preliminary results of combustion tests with the straw residue showed that the residue was combusted successfully without causing fouling problems even when the combustion temperature reached 1600° C., as compared to the fact that raw rice straw usually starts to cause the fouling problems at 1400° C. (Jenkins, B. M., Net Energy Analysis, EBS 216 Class Handout, University of California at Davis (1997)). The average heating value of the residues tested was 14.44 MJ/Kg, as compared to 14.75 MJ/Kg for raw rice straw.

TABLE 6

| Rice straw | N (%) | P (%) | K (%) | Ca (%) | Cl (%) | Mg (%) | S (%) | Na (%) | C (%) |
|---|---|---|---|---|---|---|---|---|---|
| Before digestion | 0.457 | 0.09 | 1.58 | 0.24 | 0.87 | 0.21 | 0.028 | 0.023 | 34.8 |
| After digestion | 0.947 | 0.11 | 0.16 | 0.28 | 0.11 | 0.14 | 0.016 | 0.017 | 32.7 |

Note: The reported content is percentage of dry matter (total solids).

1.2f Operation of APS-Digester System for Continuous Biogas Production

Figure 13:
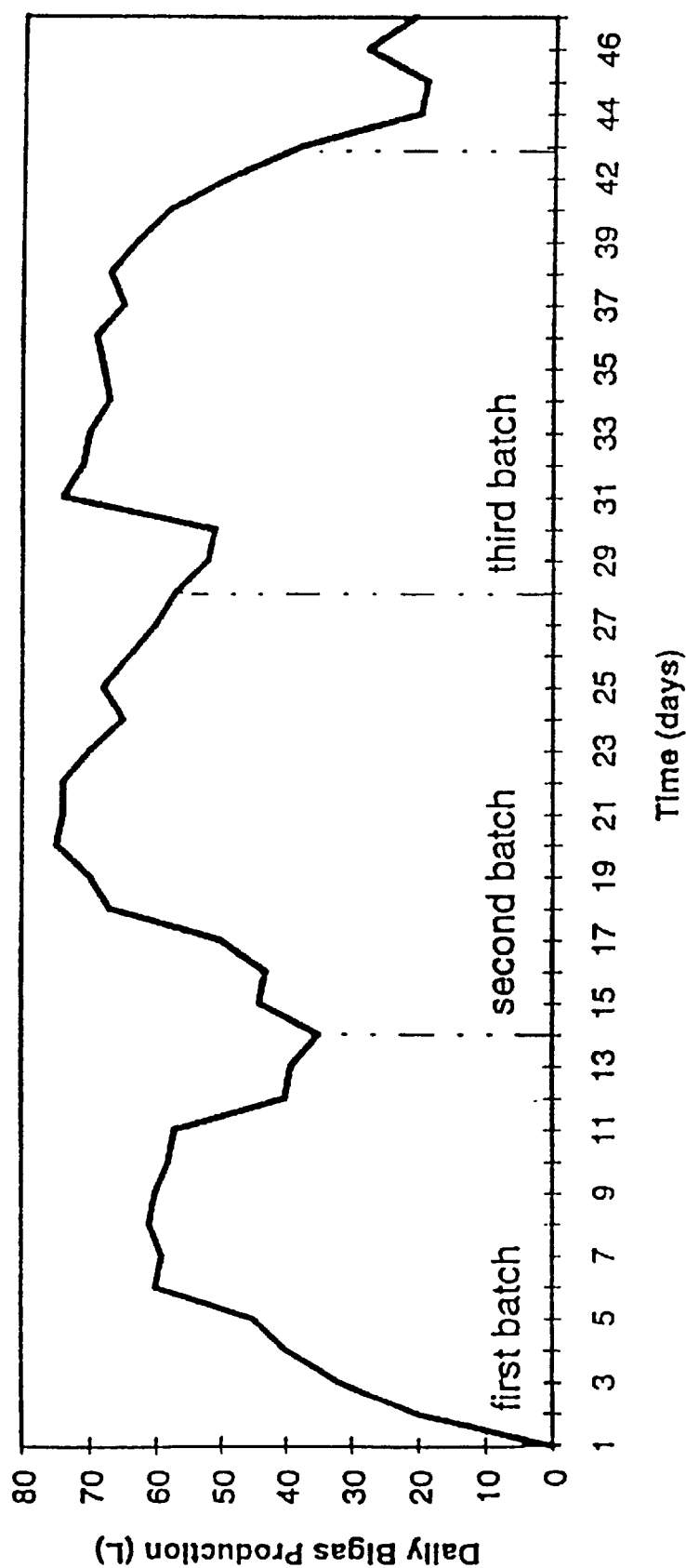
FIG. 13 displays the biogas production of a prototype APS-digester system with two hydrolysis reactors and one biogasification reactor for digestion of rice straw (chopped and 25 mm).

Batch digestion tests reported as above have shown the feasibility of using the APS-Digester for biogasification of rice straw with a supplement of nitrogen source, such as ammonia. Batch digestion is featured with cyclic biogas production. In practical applications, the APS-Digester system may be designed to use more than one hydrolysis reactor to couple with the biogasification reactor so that the space of biogasification reactor can be utilized more efficiently and the biogas production can be maintained at a relatively constant level, which is normally required by the operation of an engine-generator system for electrical power generation. From the daily biogas production data of batch digestion runs (FIGS. 3, 7, 8 and 11), we can see that the digestion rate of each batch of rice straw was slowed down after about 14 days. Introducing a new batch of feedstock at this time will sustain the biological activities in the digestion system, especially in the biogasification reactor, so to keep the biogas production continuously at a high level. FIG. 13 shows the biogas production of a prototype APS-Digester System with two hydrolysis reactors and one biogasification reactor. The system was operated for 47 days and three batches of rice straw was digested. The straw was chopped and 25 mm long without thermal pretreatment. We can see that cyclic variation of biogas production was much damped and the biogas production was continuous. With proper design of the operational schemes in terms of feedstock loading and unloading and retention time, the APS-Digester system will become a viable and highly efficient anaerobic digestion system for biogasification of biomass materials such as rice straw.

Example 2

2.1 Materials and Methods 2.1a General

Figure 14:
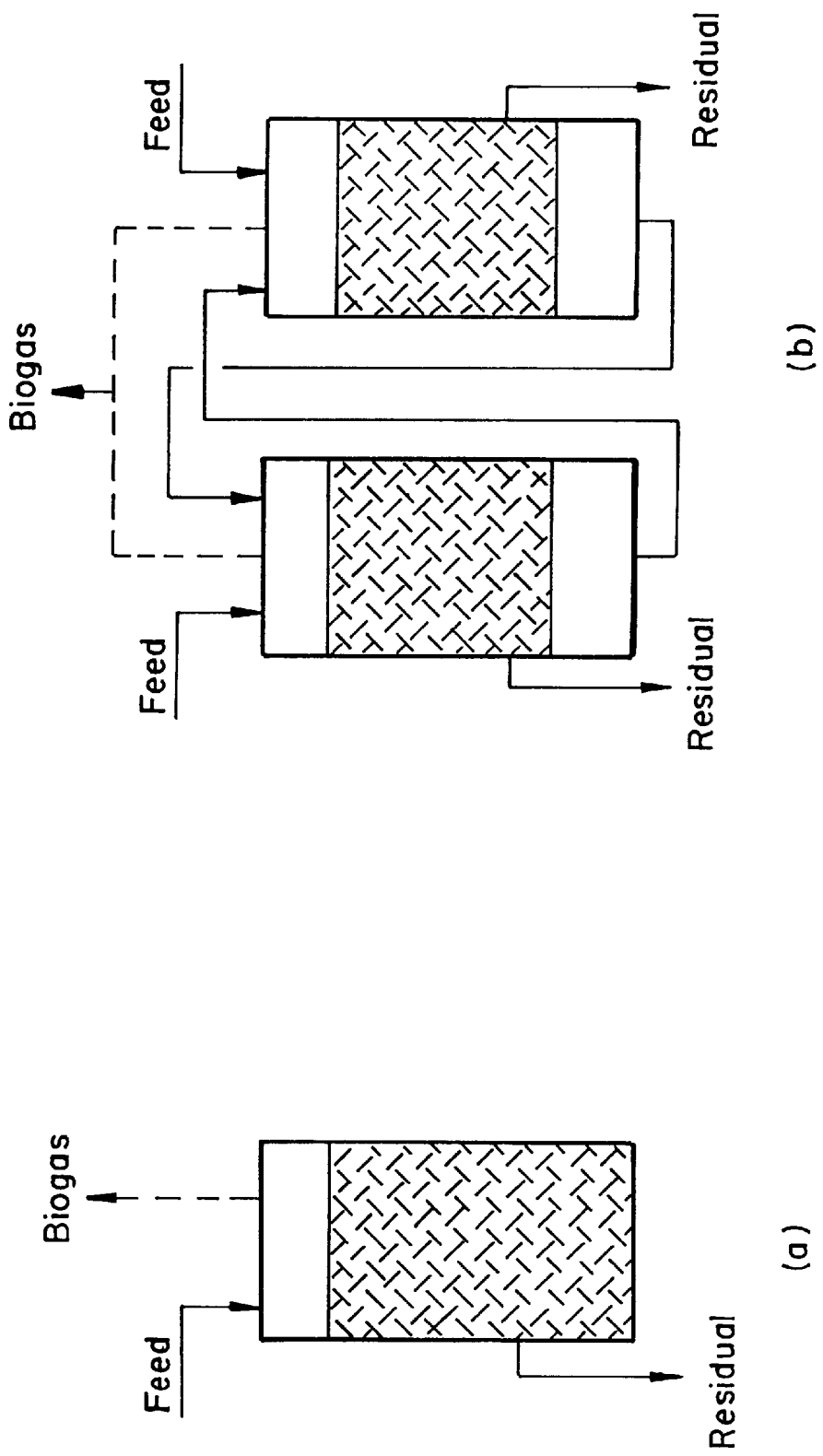
FIG. 14 is a schematic diagram of the laboratory set-up of: (a) batch; and (b) SEBAC systems.
Figure 15:
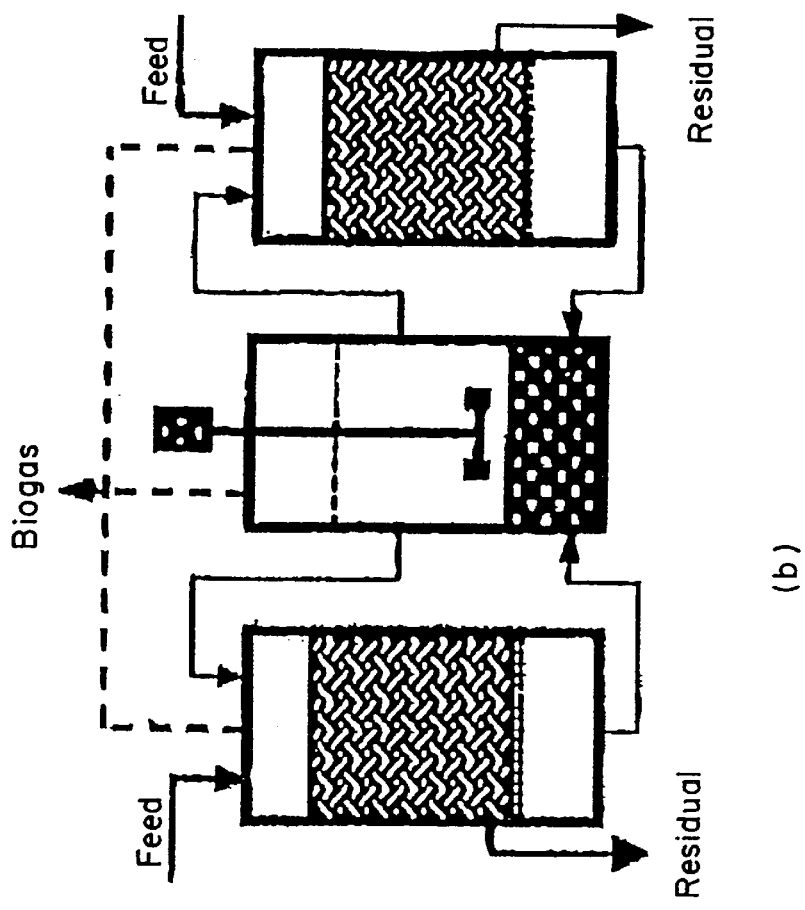
FIG. 15 is a schematic diagram of the laboratory set-up of: (a) single batch APS; and (b) multiple batch APS digesters.
Figure 15:
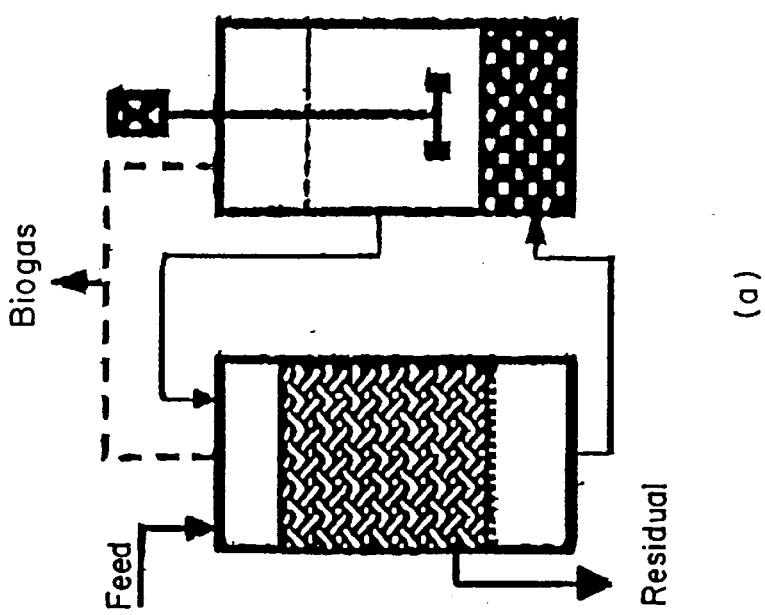

Two sets of experiments were designed to compare Batch system with the APS-Digester system using single-batch digestion and to compare SEBAC system with the APS-Digester system using multiple-batch digestion, respectively. The schematic diagrams of three digestion systems used are shown in FIGS. 14 and 15. The engineering features and operational procedures of individual systems are described as follows.

2.1b Description and Operation of Anaerobic Digestion Systems

All the anaerobic reactors used were made of plexiglass and had a total and working volume of 5.2 and 4.0 L each, respectively. All the reactors were maintained at 35±1° C. using heated circulating water jackets. Each reactor was connected to a gas collection bag and a wet-tip gas meter, which measured the biogas production (L) per day. Ammonia hydroxide solution (58%) was added to rice straw for all the digestion runs to adjust the C/N of rice straw 25 prior to digestion. Duplicative tests were performed for all the digestion runs. The data reported in this paper are the average of duplicate test runs.

The batch system was operated as a single-batch digestion system. Three different TS loading levels of 50 g/L. 75 g/L. and 100 g/L were tested. The corresponding amount of dry straw used 200 g. 300 g. and 400 g. respectively. The TS loading was defined as the amount of dry rice straw (g) loaded per unit working volume (L) of hydrolysis reactor. For each batch digestion, rice straw (chopped into 1-inch length) was mixed with anaerobic seed sludge collected from a mesophilic digester as the municipal wastewater plant in Davis, Calif. The amount of the seed sludge used was determined to provide biomass equal to 40% of volatile solids (VS) in 200 g of rice straw on a dry weight basis. Water was added to the reactor to achieve the final TS concentrations of 5%, 7.5%, and 10% for 50 g/L, 75 g/L, and 100 g/L TS loading levels, respectively. Each batch digestion proceeded for 24 days.

The SEBAC system (FIG. 14-$b$) was operated as a multiple-batch digestion system. Both reactors in the system are solid-bed reactors with a perforated steel plate placed in the lower part of each reactor to allow liquid collection at the bottom of the reactor. The first batch digestion was started with the mixture of rice straw and anaerobic seed sludge in the same way as with the Batch system described above. After 12 days, when the digestion process in the first batch was established, the second batch digester was started with the mixture of rice straw and water which had a TS concentration of 7.5%. Intermittent liquid circulation (one minute for every two hours) between two reactors at a constant flow rate of 600 mL/min was initiated as soon as the second batch was started to allow the inoculum to transfer. After 24 days, the first batch digestion was finished. The residual solids were taken out and the third batch was carried out in the same way as the second batch. A total of three batches were monitored using a digestion period of 42 days. The second and third batches of digestion were assumed to represent typical operation of a SEBAC system. The laboratory set up of the SEBAC system is presented in FIG. 14-$b$.

Two types of the APS-Digester system were used. The first system (FIG. 15-$a$) had one hydrolysis reactor and one biogasification reactor. The first system was used to compare with the Batch system and therefore operated as a single-batch digestion system. The second system was used to compare with the SEBAS system and operated as a multiple-batch digestion system. A perforated steel plate was placed in the lower part of each hydrolysis reactor to allow the liquid collection. With the first system, the biogasification reactor was initially seeded with anaerobic seed sludge to provide the Mixed Liquid Volatile it. Suspended Solid (MLVSS) of 11,000 mg/L. The hydrolysis reactor was started with rice straw and water. Liquid was recirculated between the two reactors once every two hours at a constant flow rate of 600 mL/min. Right after recirculation, the biogasification reactor was mixed for one minute and then allowed to react quiescently with biomass settled to the bottom prior to next recirculation. Three TS loading levels of 50 g/L, 75 g/L and 100 g/L were tested. The second system—the multiple-batch APS-Digester system was started in the same way as the single-batch APS-Digester system described above. After 12 days of operation with the first batch system, the second hydrolysis reactor loaded with rice straw and water was put in line. The liquid recirculation and reactor mixing sequence between the second hydrolysis reactor and the biogasification reactor was the same as in the first system but with one-hour delay. A TS loading level of 75 g/L was used in the second system to compare with the SEBAC system. The system operation was monitored for the same length of time (42 days) as with the SEBAC system.

Finally, computer simulation was performed for a model APS-Digester system with a capacity of processing one ton of dry straw per day to study the variation of daily biogas production as affected by the number of hydrolysis reactors. One biogasification reactor was coupled with different numbers of hydrolysis reactors (one, two, three, four, six, eight, and twelve). The daily biogas production data from the laboratory test with the TS loading level of 100 g/L were used in the simulation. Each system was simulated for a period of four months with a retention time of 24 days for each batch digestion. For each simulation, hydrolysis reactors were started in sequence. For example, for the system with one biogasification reactor coupled with eight-hydrolysis reactors, the batch digestion in the hydrolysis reactors was three days apart in schedule. The daily biogas production (L/day) was calculated for each simulation.

2.1c Analytical Procedure

Gas samples were taken daily from the sampling port in the gas collection line of each reactor and analyzed for the contents of methane ($CH_4$ and carbon dioxide ($CO_2$) using a Gas Chromatography (GC) equipped with a thermal conductivity detector (TCD). The liquid samples were taken from each reactor and measured for pH using a pH meter. Before and after the digestion, both liquid and solid samples from each reactor were taken to analyze for TS and VS concentrations. The reductions of TS and VS for each treatment were calculated based on mass balances. The analysis procedures of TS and VS followed the standard methods (APHA, 1992).

2.2 Results 2.2a General

The rice straw used in this study was collected in bales in northern California and transported to the laboratory. The characteristics of the rice straw as determined from three replicates are presented in Table 7. The C/N of rice straw was 76. Ammonia was therefore added to adjust the C/N to 25, which was found to be the optimum level for anaerobic digestion (Hills and Roberts, 1981**).

TABLE 7

| C (%) | N (%) | P (%) | K (%) | H (%) | S (%) | TS (%) | VS (%) | Ash (%) |
|---|---|---|---|---|---|---|---|---|
| 34.81 ± 0.44 | 0.46 ± 0.021 | 0.09 ± 0.008 | 1.58 ± 0.024 | 4.61 ± 0.05 | 0.14 ± 0.01 | 92.12 ± 0.89 | 79.50 ± 0.45 | 20.50 ± 0.21 |

Note: The contents of C, N, P, K, H, S, VS, and Ash are expressed as the percentage of TS.

2.2b Comparison of the APS-Digester with the Batch System

The daily and cumulative biogas production, methane contents of biogas, and pH variation for both APS-Digester and batch systems are presented in FIGS. 16–19. The average methane yield, methane content of biogas, and reductions of TS and VS are presented in Table 8. The methane yield with the APS-Digester system increased from 0.38 to 0.42 L/g VS added with the TS loading was increased from 50 to 100 g/L whereas the methane yield with the batch system decreased from 0.37 to 0.05 L/g VS added. The increase of the methane yield with the APS-Digester system could be explained by the ability of methanogenic bacteria in the biogasification reactor to handle a higher organic loading level. The decease of the methane yield with the batch system might be caused by the excessive accumulation of VFSs, leading to the rapid drop of pH to a level (below 6.0) that became inhibitory to the methanogenic bacteria. Therefore, the APS-Digester system showed advantages over the batch system by having higher TS and VS reductions, higher methane content of the biogas and smaller variation of pH during digestion.

Figure 16:
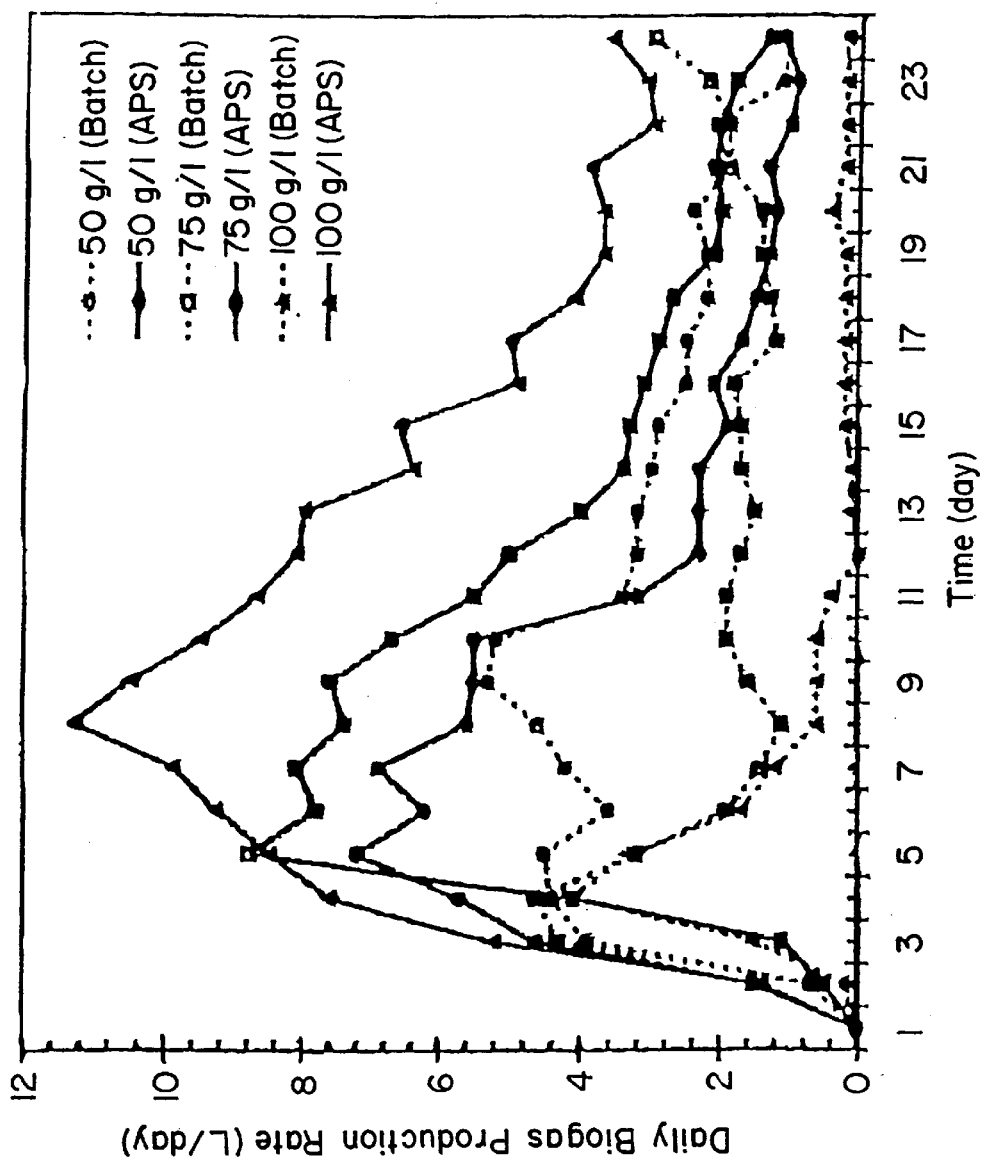
FIG. 16 displays the daily biogas production at different total solids (TS) loading levels with the APS digester and batch systems.
Figure 17:
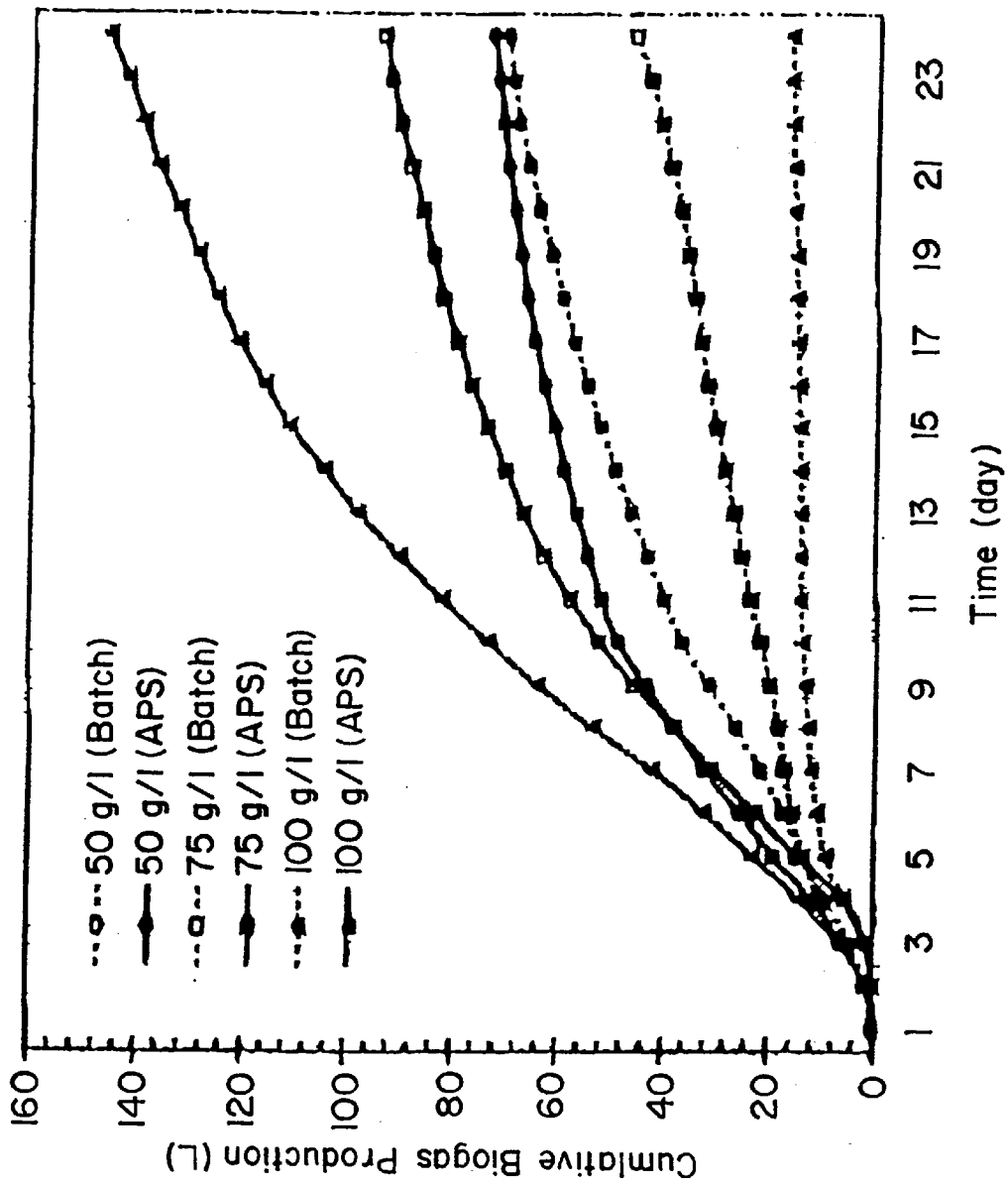
FIG. 17 displays the cumulative biogas production at different TS lading levels with the APS digester and batch systems.
Figure 18:
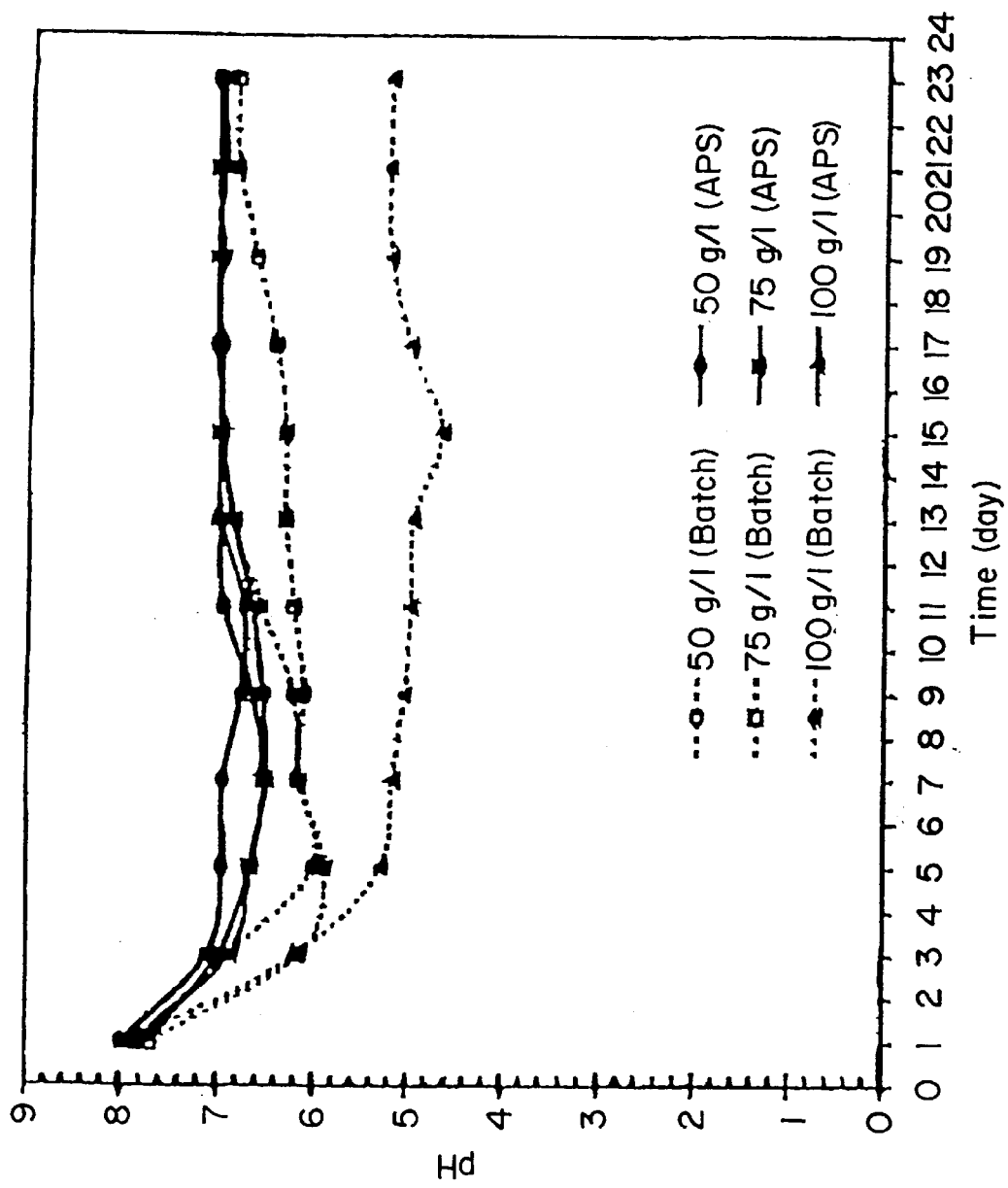
FIG. 18 displays the pH variation at different TS loading levels with the APS digester and batch systems.
Figure 19:
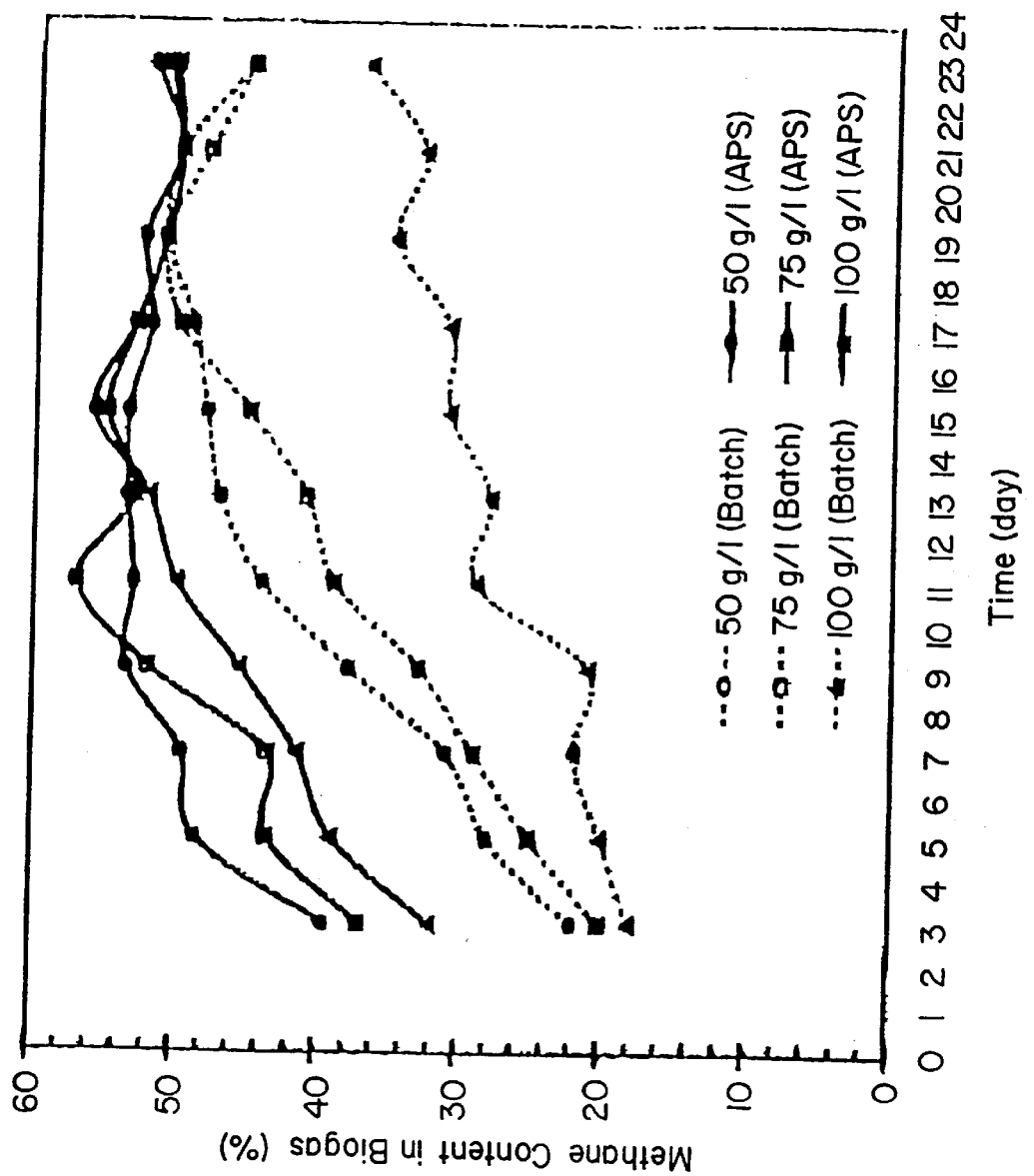
FIG. 19 displays the methane content of biogas at different TS loading levels with the APS digester and batch systems.

With the batch system, it should also be noticed that the daily biogas production rapidly increased shortly after the digestion was initiated and reached to the maximum on the fourth day for all three TS loading levels. The biogas produced during the first four days was essentially carbon dioxide ($CO_2$). This indicates that soluble sugars were released quickly during these initial period. The acetogenic bacteria were responsible for the acid and $CO_2$ production and pH decrease. When the TS loading became too high, such as at 75 g/L, accumulation of VFAs in the system lead to inhibition of methanogenic bacteria, resulting in reduced or stopped biogas production. The results showed that the TS loading in the batch system should be limited to 50 g/L. In contrast, the APS-Digester did not show VFA inhibition even at the highest loading level (100 g/L) tested. This was reflected by the daily and cumulative biogas production as shown in FIGS. 16 and 17. At higher loading levels (75 g/L and 100 g/L), the daily biogas production in the APS-Digester system was much higher during the first several days than in the batch system. The methane content of the biogas was also much higher.

TABLE 8

| Digester System | APS | | | Batch | | |
|---|---|---|---|---|---|---|
| Total Solid Loading (g/L) | 50 | 75 | 100 | 50 | 75 | 100 |
| Methane Yield (L/g VS added) | 0.38 | 0.38 | 0.42 | 0.37 | 0.19 | 0.05 |
| Methane Content in Biogas (%) | 50.10 | 49.14 | 50.60 | 41.45 | 37.63 | 27.72 |
| Total Solid Reduction (%) | 37.48 | 36.59 | 40.67 | 35.88 | 16.46 | 5.33 |
| Volatile Solids Reduction (%) | 43.18 | 44.28 | 49.14 | 47.66 | 22.51 | 8.01 | average) than the biogas from the SEBAC biogas production throughout digestion. This is because the biogasification reactor in the APS-Digester system provided buffering capacity for the system and better environmental conditions to methanogenic bacteria, resulting in higher methane production. Therefore the APS-Digester system is found to be more advantageous than the SEBAC system in terms of methane production and process stability.

TABLE 9

| Digester Performance | APS | SEBAC |
|---|---|---|
| Total Solid Loading (g/L) | 75.00 | 75.0 |
| Methane Yield (L/g VS added) | 0.34 | 0.35 |
| Methane Content (%) | 50.22 | 40.78 |
| Total Solid Reduction (%) | 35.66 | 36.21 |
| Volatile Solids Reduction (%) | 40.68 | 41.08 |

Figure 23:
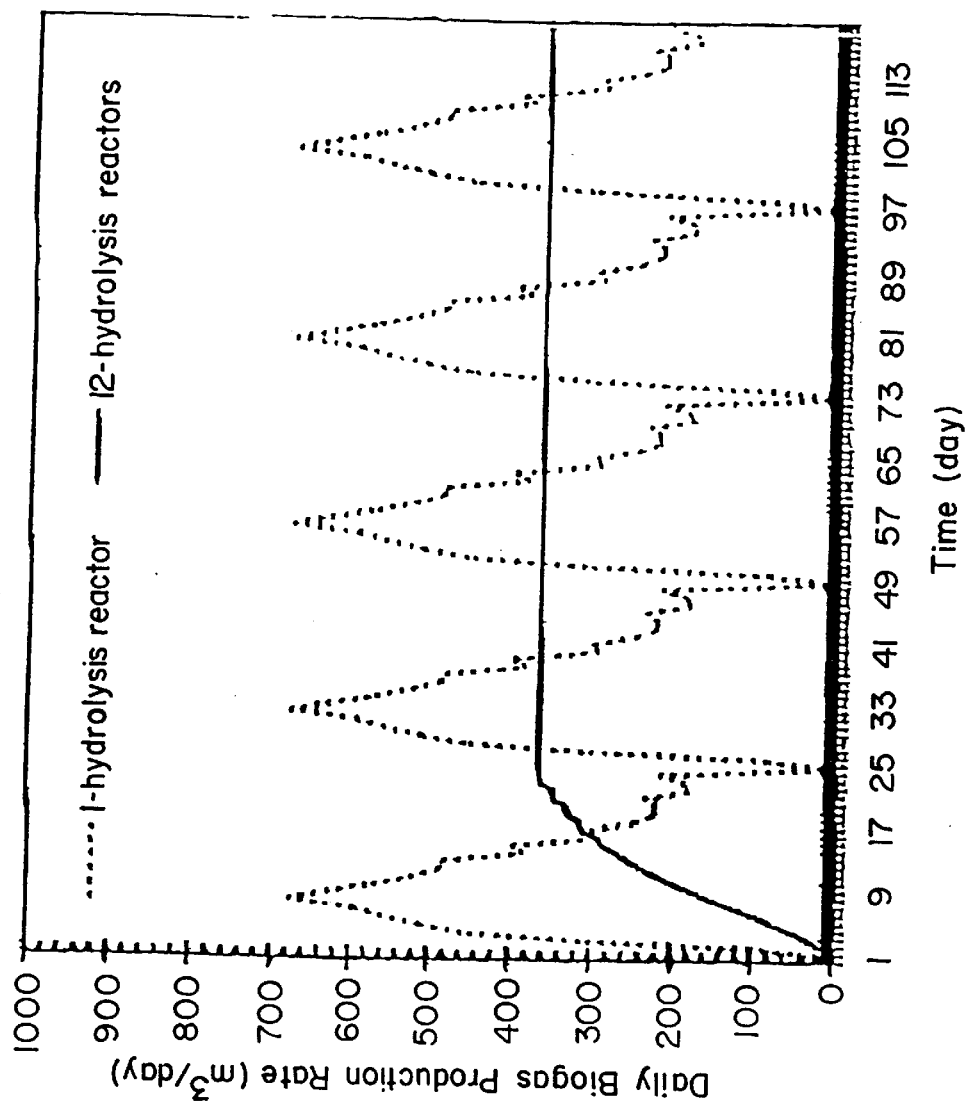
FIG. 23 displays the simulated daily biogas production of the APS digester system with one or twelve hydrolysis reactors.
Figure 24:
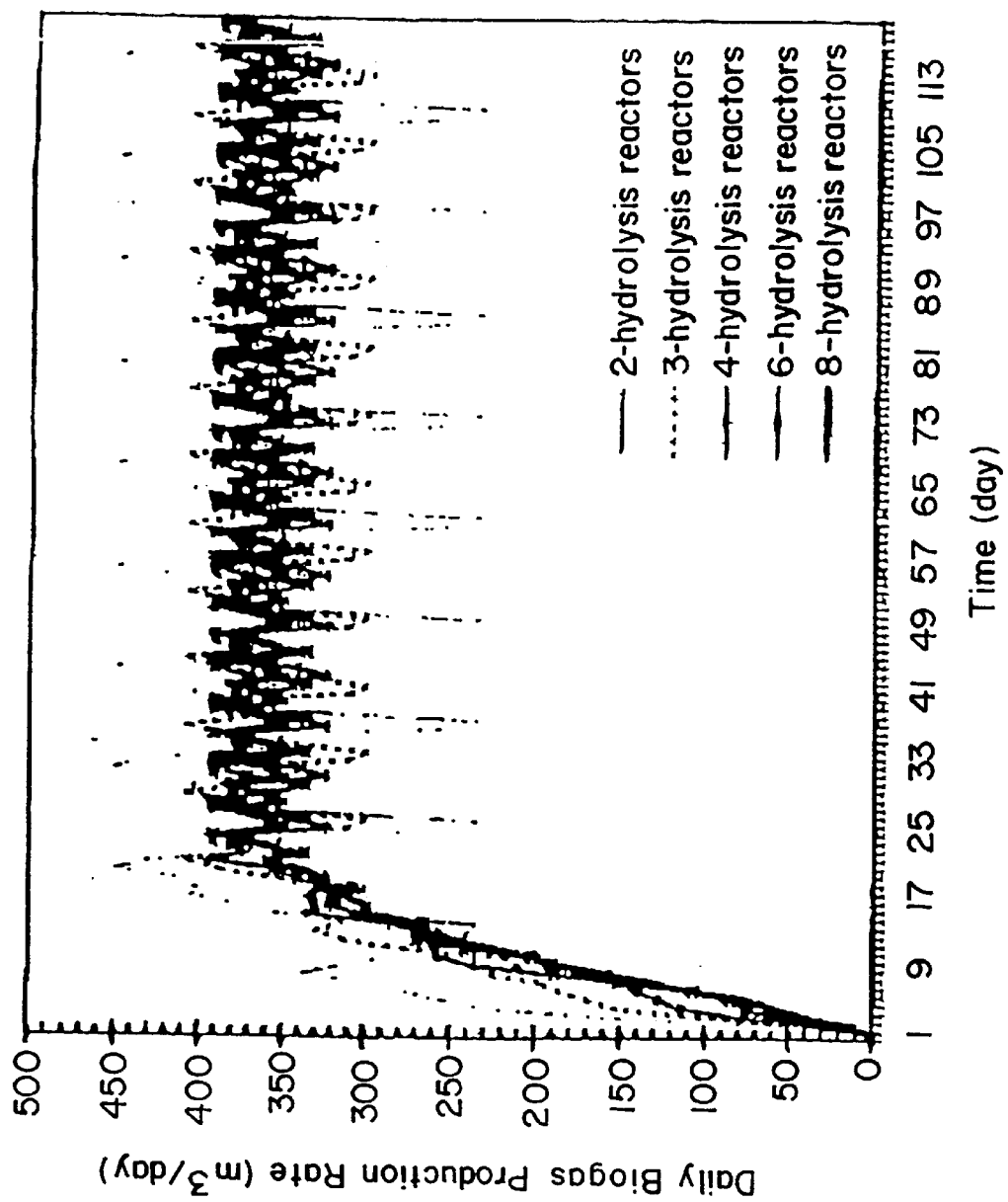
FIG. 24 displays the simulated daily biogas production of the APS digester system with two, three, four, six and eight hydrolysis reactors.

2.2d Computer Simulation of the APS-Digester System for Best Design Configurations Computer simulation was conducted to analyze the biogas production profile of the APS-Digester system with one biogasification reactor coupled with different numbers of hydrolysis reactors. The predicted daily biogas production with one biogasification reactor coupled with one, two, three, four, six, eight, and twelve hydrolysis reactors are presented in FIGS. 23–24 and the predicted average daily biogas production and its variance are presented in Table 10. The variation of daily biogas production became smaller with the increase of the number of hydrolysis reactors. With the processing capacity of 1 ton/day, the daily biogas production was 365 m³/day for all the combinations after a start-up period of 24 days. However, the variations of daily biogas production decreased from 17.77% to 4.05% and 0.14% when the numbers of hydrolysis reactors were increased from two to eight and twelve, respectively. The least variation in daily biogas production was achieved with one biogasification reactor coupled with twelve hydrolysis reactors.

TABLE 10

| Num. of Hydrolysis Reactors | 1 | 2 | 3 | 4 | 6 | 8 | 12 |
|---|---|---|---|---|---|---|---|
| Ave. Daily Biogas (m³/day) | 365.00 | 365.00 | 365.00 | 365.00 | 365.00 | 365.00 | 365.00 |
| Standard Deviation (m³) | ±179.82 | ±64.86 | ±38.23 | ±24.06 | ±20.09 | ±14.78 | ±0.50 |
| Std. Dev./Average (%) | 49.27 | 17.77 | 10.47 | 6.59 | 5.50 | 4.05 | 0.14 |

2.2c Comparison of the APS-Digester with SEBAC Systems

Figure 20:
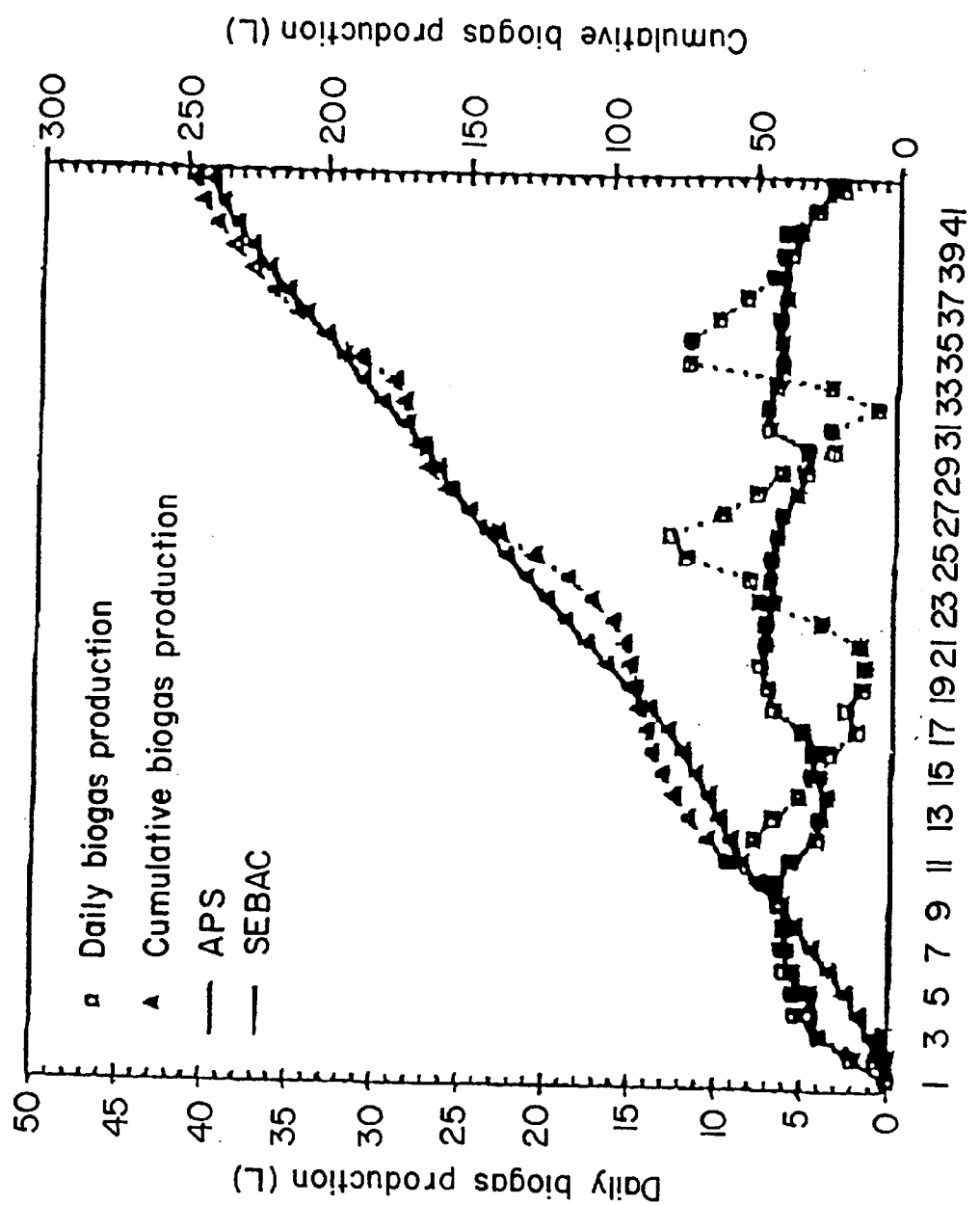
FIG. 20 displays the daily and cumulative biogas production at 75 g/L TS loading with the APS digester and SEBAC systems.
Figure 21:
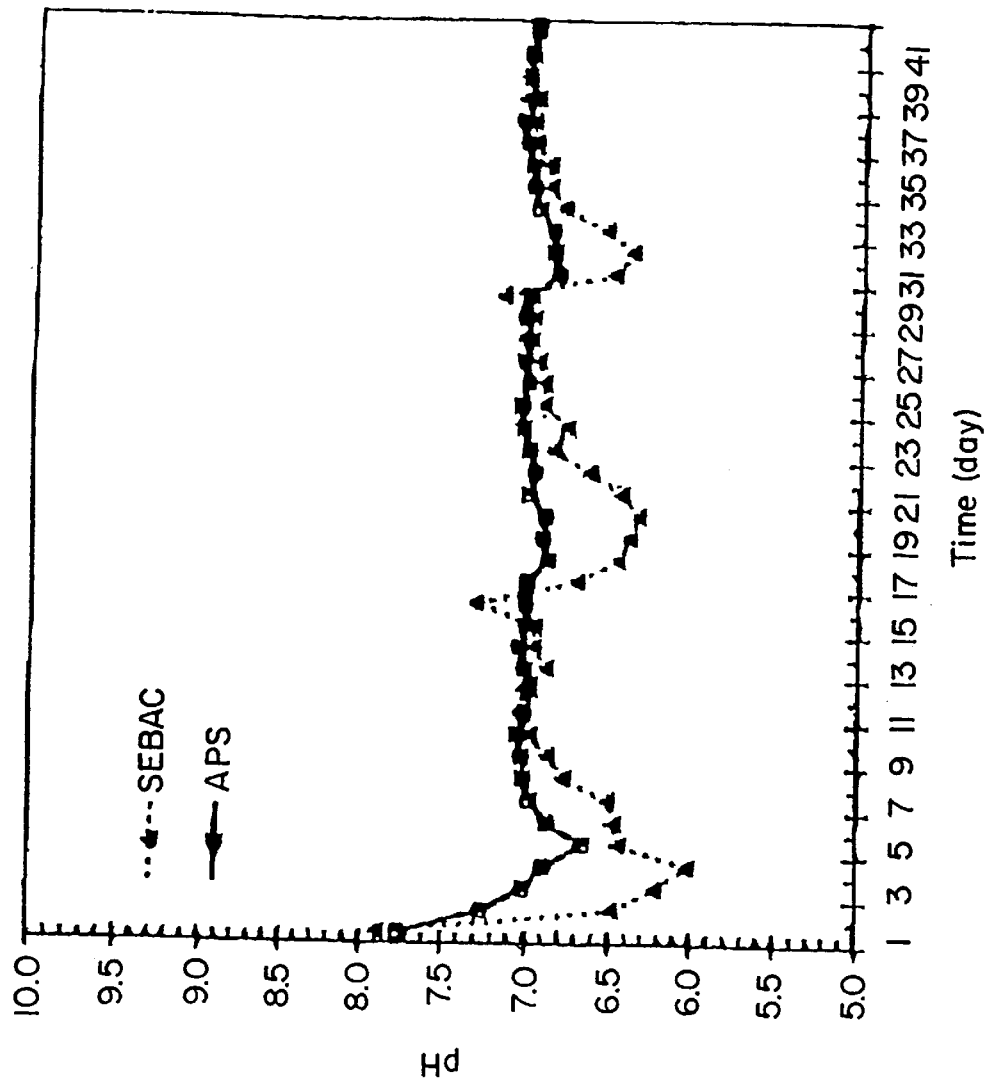
FIG. 21 displays the pH variation at 75 g/L TS loading with the APS digester and SEBAC systems.
Figure 22:
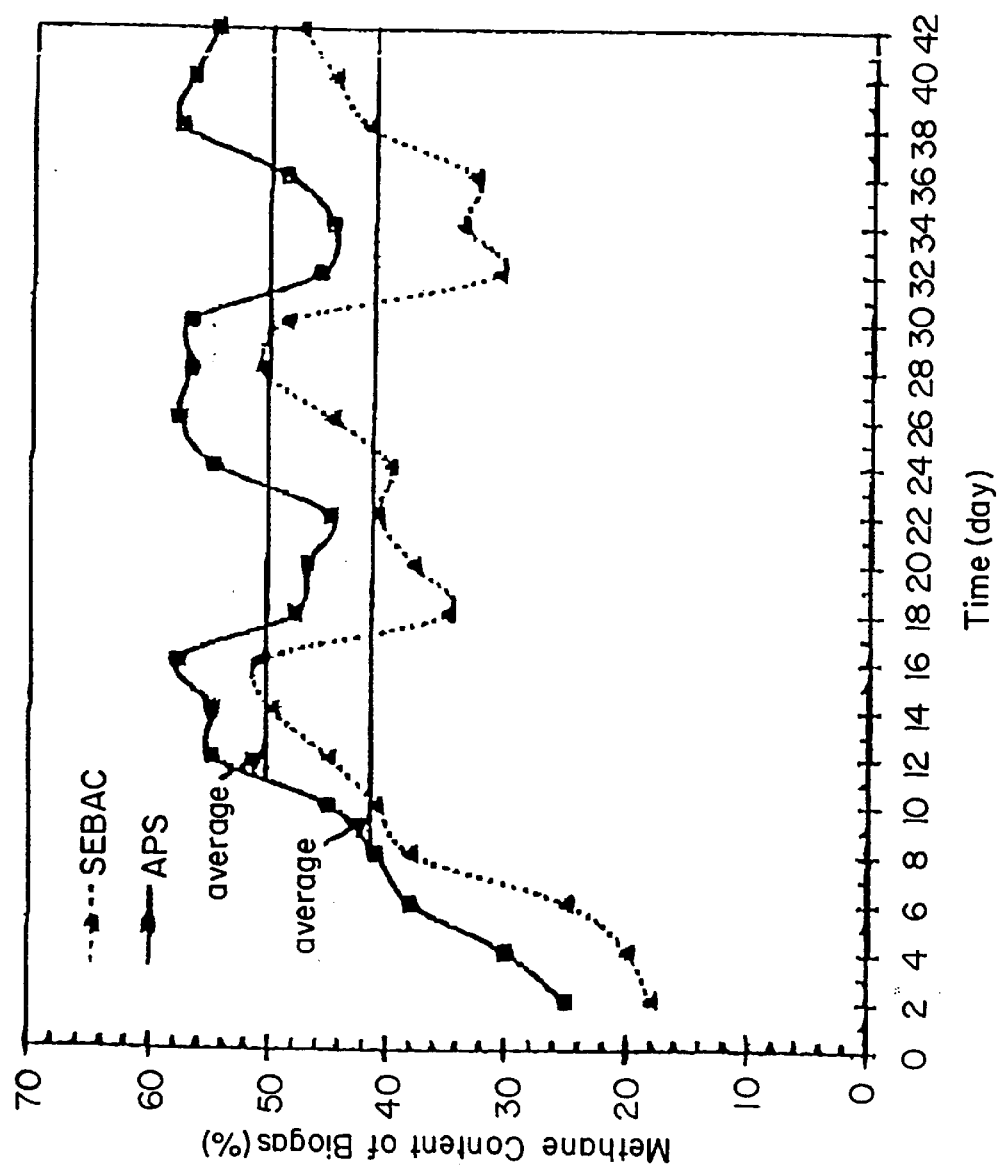
FIG. 22 displays the methane content of the biogas at 75 g/L TS loading with the APS digester and the SEBAC systems.

The daily and cumulative biogas production, methane content of biogas, and pH variation during digestion are presented in FIGS. 20–22. The pH of the APS-Digester system was measured to be the pH in the biogasification reactor. The average methane yield, methane content, and reductions of TS and VS are presented in Table 9. The two systems achieved similar methane yield and reductions of TS and VS. However, the biogas produced from the APS-Digester system had higher methane content (50.22% on It is to be understood that the above description and is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which the claims are entitled. The disclo-

What is claimed is:

1. A method for producing methane by digesting solid agricultural waste having methane generating potential, said method comprising:

(a) a hydrolysis phase comprising;
   (i) contacting said solid agricultural waste with a hydrolytic bacterial culture in a hydrolysis vessel separated into a lower chamber and an upper chamber by a filtration means preventing passage of said solid agricultural waste from said upper chamber into said lower chamber;
   (ii) incubating said solid agricultural waste and said hydrolytic bacterial culture at a pH of from about 4.5 to about 6.5, thereby hydrolyzing said solid agricultural waste to form an aqueous hydrolysis mixture comprising volatile fatty acids, said aqueous hydrolysis mixture and the solid agricultural waste being retained in said hydrolysis vessel throughout said incubating;
   (iii) following said incubating, filtering at least a portion of said aqueous hydrolysis mixture through said filtration means into said lower chamber, separating said aqueous hydrolysis mixture from the solid agricultural waste, thereby forming a liquid methanogenesis feedstock essentially free of the solid agricultural waste;

(b) a methanogenesis phase comprising;
   (i) transferring from said lower chamber of said hydrolysis vessel at least a portion of said liquid methanogenesis feedstock into a methanogenesis reactor where said feedstock is contacted with a methanogenic bacterial culture contained in said methanogenesis reactor, thereby forming a methanogenesis mixture having a pH of from about 6.5 to about 7.5;
   (ii) incubating said methanogenesis mixture, thereby forming methane, said methanogenesis mixture being retained in said methanogenesis reactor throughout said incubation;
   (ii) collecting said methane formed in step (b(ii));
   (iv) transferring at least a portion of said methanogenesis mixture from said methanogenesis reactor into said hydrolysis vessel where said methanogenesis mixture is contacted with said solid agricultural waste;

(c) a recycling phase comprising;
   (i) repeating steps (a(i)–a(ii)) and steps (b(i)–(iv)), to further hydrolyze the solid agricultural waste in sad hydrolysis vessel and continuously generate methane in said methanogenesis reactor, thereby exhausting said methane generating potential of the solid agricultural waste, and forming depleted agricultural waste;

(d) following said recycling phase, removing at least a portion of said depleted agricultural waste from said hydrolysis vessel, while said methanogenesis reactor continues to generate methane; and (e) optionally, following step (d), introducing a batch of solid agricultural waste into said hydrolysis reactor, and repeating steps (a(i)–a(ii)), steps (b(i)–(iv)) and step (c).

* * * * *